(12) United States Patent
Chaum et al.

(10) Patent No.: US 11,686,722 B2
(45) Date of Patent: Jun. 27, 2023

(54) COMPOSITIONS AND METHODS TO DETECT MOLECULES IN A SAMPLE

(71) Applicant: Infusense Corp., Memphis, TN (US)

(72) Inventors: Edward Chaum, Memphis, TN (US); Erno Linder, Memphis, TN (US)

(73) Assignee: INFUSENSE CORP., Nashville, TN (US)

( * ) Notice: Subject to any disclaimer, the term of this patent is extended or adjusted under 35 U.S.C. 154(b) by 0 days.

(21) Appl. No.: 16/470,373

(22) PCT Filed: Dec. 18, 2017

(86) PCT No.: PCT/US2017/066997
§ 371 (c)(1),
(2) Date: Jun. 17, 2019

(87) PCT Pub. No.: WO2018/112458
PCT Pub. Date: Jun. 21, 2018

(65) Prior Publication Data
US 2019/0331656 A1 Oct. 31, 2019

Related U.S. Application Data

(60) Provisional application No. 62/435,530, filed on Dec. 16, 2016.

(51) Int. Cl.
G01N 33/487 (2006.01)
G01N 27/327 (2006.01)
G01N 27/403 (2006.01)
G01N 33/94 (2006.01)

(52) U.S. Cl.
CPC ... *G01N 33/48707* (2013.01); *G01N 27/3275* (2013.01); *G01N 27/403* (2013.01); *G01N 33/948* (2013.01)

(58) Field of Classification Search
None
See application file for complete search history.

(56) References Cited

U.S. PATENT DOCUMENTS

| | | |
|---|---|---|
| 8,549,318 B2 | 10/2013 | White et al. |
| 9,700,246 B2 | 7/2017 | Chaum et al. |
| 9,983,162 B2 | 5/2018 | Chaum et al. |
| 2001/0025151 A1 | 9/2001 | Kimball et al. |
| 2006/0173256 A1 | 8/2006 | Ridder et al. |
| 2011/0050431 A1 | 3/2011 | Hood et al. |

(Continued)

FOREIGN PATENT DOCUMENTS

| | | | |
|---|---|---|---|
| DE | 102012202649 | 8/2013 | |
| WO | WO-2010045465 A1 * | 4/2010 | ......... A61B 5/14546 |

(Continued)

OTHER PUBLICATIONS

G. Rocchitta, et al., "Enzyme Biosensors for Biomedical Applications: Strategies for Safeguarding Analytical Performances in Biological Fluids", Sensors, 16(6): p. 780, May 2016.*

(Continued)

*Primary Examiner* — J. Christopher Ball
(74) *Attorney, Agent, or Firm* — Baker Donelson

(57) ABSTRACT

This invention is directed to non-invasive devices and methods to detect electrochemically active molecules in a fluid sample of a subject.

35 Claims, 13 Drawing Sheets

(56) References Cited

U.S. PATENT DOCUMENTS

| | | | |
|---|---|---|---|
| 2011/0152646 A1* | 6/2011 | Anderson | A61B 5/1459 600/310 |
| 2012/0116195 A1 | 5/2012 | Chaum et al. | |
| 2012/0122229 A1 | 5/2012 | Kampouris et al. | |
| 2013/0124036 A1 | 5/2013 | Varga et al. | |
| 2013/0168175 A1* | 7/2013 | Polzius | A61B 10/0045 180/272 |
| 2013/0203065 A1 | 8/2013 | Ettlinger et al. | |
| 2014/0124383 A1 | 5/2014 | Miyahara et al. | |
| 2015/0119848 A1 | 4/2015 | Chaum et al. | |
| 2016/0022185 A1 | 1/2016 | Agarwal et al. | |

FOREIGN PATENT DOCUMENTS

| | | | | |
|---|---|---|---|---|
| WO | WO-2014120979 A1 * | 8/2014 | | G01N 33/54386 |
| WO | 2016/028497 | 2/2016 | | |

OTHER PUBLICATIONS

International Search Report for PCT/US2017/066997 dated Mar. 6, 2018.

Written Opinion of the ISA for PCT/US2017/066997 dated Mar. 6, 2018.

Alozie, SO, Martin BR, Harris LS, et al. 3H-delta 9-Tetrahydrocannabinol, 3H-cannabinol and 3H-cannabidiol: penetration and regional distribution in rat brain. Pharmacol Biochem Behav 1980; 12: 217-21.

Arumugam et al., "Wafer-scale fabrication of patterned carbon nanofiber nanoelectrode arrays: A route for development of multiplexed, ultrasensitive disposable biosensors," Biosensors Bioelectronics 24(9): 2818-2824 (2009).

Atakan, Zerrin. Cannabis, a complex plant: different compounds and different effects on individuals. Therapeutic advances in psychopharmacology 2.6 (2012): 241-254.

Balbino MA, Eleoterio IC, de Oliveira LS, de Menezes MMT, de Andrade JF, Ipolito AJ, de Oliveira MF. A comparative study between two different conventional working electrodes for detection of ?9 -tetraydrocannabinol using square-wave voltammetry: a new sensitive method for forensic analysis. J. Braz Chem Soc. 2014;25:589-596.

Bard and Falkner, Electrochemical Methods, John Wiley and Sons, New York (2001).

Blanco et al., "Microfluidic-optical Integrated CMOS Compatible Devices for Label-free Biochemical Sensing," J Micromechanics Microengineering 16:1006-1016 (2006).

Chen and Lee, "A Bonding Technique using Hydrophilic SU-8," J Micromechanics Microengineering 17:1978-1984 (2007).

Delamarche et al., Stability of Molded polydimethylsiloxane,: Adv. Materials 9:741-746 (1997).

ElSohly, Mahmoud A., and Desmond Slade. "Chemical constituents of marijuana: the complex mixture of natural cannabinoids." Life sciences 78.5 (2005): 539-548.

Fletcher et al., "Transfer of Flexible Arrays of Vertically Aligned Carbon Nanofiber Electrodes to Temperature-Sensitive Substrates," Adv. Mat. 18(13):1689-1694 (2006).

Grotenhermen, F. Pharmacokinetics and Pharmacodynamics of Cannabinoids; Clin Pharmacokinet 2003;42 (4):327-360.

Huang et al., Microelectrode Arrays for Electrochemistry: Approaches to Fabrication, Small 5(7):776-788 (2009).

Kivlehan et al., Toward Feedback-Controlled Anesthesia: Voltammetric Measurement of Propofol in Serum-Like Electrolyte Solutions. Analytical Chemistry (2012).

Kivlehan F, Chaum E, Lindner E. Propofol Detection and Quantification in Human Blood: The Promise of Feedback Controlled, Closed-loop anesthesia. Analyst, 2014, 140(1):98-106.

Langmaier J, Garay F, Kivlehan F, Cham E, Lindner E. Electrochemical Quantification of 2,6-Diisopropylphenol (Propofol), Analytica Cheimica Acta, 2011, 704:63-67.

Lee and Voros, "An Aqueous-based Surface Modification of poly(dimethylsiloxane) with poly(ethylene glycol) to Prevent Biofouling," Langmuir 21:11957-11962 (2004).

Matsunaga T, Iwawaki Y, Watanabe K, et al. Metabolism of delta 9-tetrahydrocannabinol by cytochrome P450 isozymes purified from hepatic microsomes of monkeys. Life Sci 1995:56(23-24):2089-95.

McDonald et al., "Fabrication of Microfluidic Systems in poly(dimethylsiloxane)," Electrophoresis 21:27-40 (2000).

Melechko et al., "Vertically aligned carbon nanofibers and related structures: Controlled synthesis and directed assembly," J. Appl. Phys. 97(4):041301 (2005).

Mijatovic et al., "Technologies for Nanofluidic Systems: Top-down vs. Bottom-up—A Review," Lab on a Chip 5:492-500 (2005).

Myers, et al, "A Feedback Control Approach to Organic Drug Infusions Using Electrochemical Measurement." IEEE Transactions on Biomedical Engineering 63.3 (2016): 506-511.

Nissim, R, Compton RG. Absorptive stripping voltammetry for cannabis detection. Chem Cent J. 2015;9:41.

Nordstrom et al., "Rendering SU-8 Hydrophilic to Facilitate use in Micro Channel Fabrication," J Micromechanics Microengineering 14:1614-1617 (2004).

Novak I, Mlakar M, Komorsky-Lovric S. Voltammetry of immobilized particles of cannabinoids. Electroanalysis. 2013;25:2631-2636.

Potje-Kamloth et al., "Electrochemically Prepared Insulation for Carbon Fiber Microelectrodes," Berichte der Bunsengesellschaft fur Physikalische Chemie 93(12):1480-1485 (1989).

Rainey F, Kivlehan F, Chaum E, Lindner E. Toward Feedback Controlled Anesthesia: Automated Flow Analytical System for EC Monitoring of Propofol in Serum Solutions. Electroanalysis, 2014, 26:1295-1303.

Toth, et al., "Electrochemical Detection in liquid Flow Analytical techniques: Characterization and Classification," Pure Appl. Chem. 76(6):1119-1138 (2004).

Unger et al., "Monolithic Microfabricated Valves and Pumps by Multilayer Soft Lithography," Science 288:113-116 (2000).

Wall ME, Sadler BM, Brine D, et al. Metabolism, disposition, and kinetics of delta-9-tetrahydrocannabinol, in men and women. Clin Pharmacol Ther 1983;34(3):352-63.

Wanklyn C, Burton D, Enston E, et al. Disposable screen printed sensor for the electrochemical detection of delta-9-tetrahydrocannabinol in undiluted saliva Chemistry Central Journal. 2016; 10:1.

Watanabe K, Matsunaga T, Yamamoto I, et al. Involvement of CYP2C in the metabolism of cannabinoids by human hepatic microsomes from an old woman Biol Pharm Bull 1995; 18(8):1138-41.

Ymeti et al., "Integration of Microfluidies with a Four-channel Integrated Optical Young Interferometer Immunosensor," Biosens. Bioelectron. 20:1417-1421 (2005).

* cited by examiner

COMPOSITIONS AND METHODS TO DETECT MOLECULES IN A SAMPLE

This application claims priority from U.S. Provisional Application No. 62/435,530 filed on Dec. 16, 2016, the entire contents of which is incorporated herein by reference.

All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

FIELD OF THE INVENTION

This invention is directed to non-invasive devices, systems, and apparatus to detect electrochemically active molecules in a fluid sample of a subject, and methods of use thereof.

BACKGROUND OF THE INVENTION

Decreasing crashes, injuries, and fatalities from impaired driving is a priority for the NHTSA as more states move toward legalizing medicinal and recreational use of marijuana. Determination that a drug (such as THC or propofol) is present in the body of a suspected drug-impaired driver close-in-time to the driving event is a critical, unmet need for law enforcement.

SUMMARY OF THE INVENTION

The present invention provides a non-invasive device for detecting at least one electrochemically active molecule in a sample of a subject, the device comprising a non-invasive, electrochemical, voltammetric sensor, wherein a voltammetric signal is generated by the sensor in the presence of an electrochemically active molecule in the sample.

Embodiments further provide for a non-invasive device for detecting at least one electrochemically active molecule in a sample of a subject, the device comprising a non-invasive sensing unit and a control unit, wherein the sensing unit comprises an electrochemical, voltammetric sensor, wherein the control unit comprises an output element, and wherein the sensing unit is in communication with the control unit. In embodiments, the sensing unit can communicate wirelessly or can be hardwired. In embodiments, the sensing unit is disposable. In embodiments, a voltammetric signal is generated by the sensor in the presence of an electrochemically active molecule, wherein the sensor communicates the voltammetric signal to the control unit, and wherein the output element of the control unit indicates the voltammetric signal, the presence of the molecule in the sample, the concentration or amount of the molecule in the sample, the identification of the molecule in the sample, or a combination thereof.

Further embodiments provide for a non-invasive device for measuring, quantifying, distinguishing, and identifying at least one electrochemically active molecule in a sample of a subject. In embodiments, the electrochemically active molecule can be any molecule that generates a signal by the sensor. Non-limiting examples of such molecules comprise a hydrophobic molecule, a lipophilic molecule, or a combination thereof, examples of which are described herein. In embodiments, the molecule comprises any molecule that generates an electrochemical voltammetric signal using the sensor and methods as described herein.

In embodiments, the electrochemical, voltammetric sensor comprises two or more electrodes oriented in parallel. For example, the sensor can comprise 2, 3, 4, 5, 6, 7, 8, 9, 10 sensors oriented in parallel. In embodiments, at least one end of the electrodes is in direct contact with a water-immiscible coating, whereas in other embodiments, the entirety of the electrodes are in direct contact with a water-immiscible coating. For example, the entirety of the outer surface of the electrodes are in direct contact with a water-immiscible coating. In embodiments, about 5%, about 10%, about 25%, about 50%, about 75%, about 90%, about 91%, about 92%, about 93%, about 94%, about 95%, about 96%, about 97%, about 98%, about 99%, or 100% of the electrodes' outer surface is in direct contact with a water-immiscible coating.

In embodiments, the electrodes comprise carbon, glassy carbon, silver, mercury, gold, platinum, palladium, ruthenium, or a combination thereof. For example, the working electrode comprises carbon, the reference electrode comprises silver, the counter electrode comprises platinum, or any combination thereof.

In embodiments, the electrodes comprise a working electrode, a reference electrode, a counter electrode, or any combination thereof. In embodiments, the working-, counter-, and reference electrodes, are completely coated and in direct contact with the water-immiscible coating.

In embodiments, the water-immiscible coating comprises a structural component, a water-immiscible organic solvent, a charge transfer component, or any combination thereof. In embodiments, the coating comprises about 15 to about 67 wt percent structural component, about 33 to about 85 wt percent water-immiscible organic solvent, and about 0.001 to about 15 wt percent charge transfer component.

In embodiments, the structural component comprises polyvinylchloride (PVC), silicone rubber, polyurethane, acrylate polymer, (meth)acrylate polymer, polypyrrole, polythiophene, polyoctylthiophene, polyanaline, polyvinyl pyrrolidone, and combinations thereof. In embodiments, the coating comprises agarose, hydrogel, sol-gel materials. If desired, the coating can comprise water-miscible components.

In embodiments, the water-immiscible organic solvent comprises 2-nitrophenyl octyl ether (o-NPOE), dioctyl sebacate (DOS), bis(2-ethylhexyl) sebacate, benzyl 2-nitrophenyl ether, bis(1-butylpentyl) adipate, bis(2-ethylhexyl) adipate, bis(2-ethylhexyl) phthalate, 1-chloronaphthalene, chloroparaffin, 1-octanol, 1-decanol, dibutyl phthalate, dibutyl sebacate, dibutyl-dilaurate, dodecyl 2-nitrophenyl ether, and combinations thereof.

In embodiments, the charge transfer component comprises tetradecylammonium tetrakis(pentofluorophenyl)borate (TDATPFPB).

Embodiments comprise a cation exchange component, such as tetrahexylammonium perchlorate, an anion exchange component, tetrahexylammonium perchlorate, or a combination thereof.

In embodiments, the coating further comprises an adhesion enhancing component, a biocompatibility enhancing component, a membrane-resistance controlling component, an anti-inflammatory agent, an anti-coagulant agent, and ion-exchange component, or a combination thereof.

In embodiments, any suitable adhesion enhancing component can be utilized in the coating.

In embodiments, any suitable biocompatibility enhancing component can be utilized in the coating. Non-limiting examples of biocompatibility enhancing components comprise nitric-oxide releasing sol-gel materials, N-(6-aminohexyl)aminopropyltrimethoxysilane, balanced isobutyltrimethoxysilane diazeniumdiolate, and combinations thereof. In embodiments, these can be used in amounts up to about 5 wt. percent, for example between about 0.001 to about 3 wt. percent.

In embodiments, any suitable anti-inflammatory agents can be utilized in the coating. These can be used in amounts up to about 5 wt. percent, for example between about 0.001 to about 3 wt. percent. These agents should not interfere with the electrochemical signal caused by partitioning of the drug into the coating.

In embodiments, any suitable anti-coagulant agents can be utilized in the coating. These can be used in amounts up to about 5 wt. percent, for example between about 0.001 to about 3 wt. percent. These agents should not interfere with the electrochemical signal caused by partitioning of the drug into the coating.

In embodiments, the structural component is PVC, the water-immiscible organic solvent is o-NPOE or DOS, and the charge transfer component is TDATPFPB. For example, the coating comprises about 15 to about 67 wt percent PCT, about 33 to about 85 wt percent o-NPOE or DOS, and about 0.001 to about 15 wt percent TDATPFPB.

In embodiments, the sample may comprise a biological sample obtained from a subject. For example, the biological sample may be a biological fluid, a biological solid, or a biological semi-solid. In embodiments, the sample may comprise saliva, lavage, tears, blood, sera, plasma, sweat or urine. the sample comprises a biological fluid.

In embodiments, the biological sample, such as a biological fluid, comprises an amount or volume sufficient generate a voltammetric signal by the sensor. For example, the amount or volume sufficient to generate a voltammetric signal may comprise a volume or amount sufficient to immerse the sensor or a portion thereof. In embodiments, the volume of the biological fluid comprises about 0 to about 1 µl, about 1 µl to about 10 µl, about 10 µl to about 50 µl, or greater than about 50 µl. In embodiments, the volume of the biological fluid comprises about 1 ml or less, about 1 to about 10 ml, or greater than 10 ml.

In embodiments, the coating or a portion thereof is in direct contact with the sample. For example, the portion of the coating that is in direct contact with the sample comprises at least about 25%, at least about 50%, at least about 75%, at least about 100% of the coating is in direct contact with the sample.

In embodiments, the sensor can be manufactured to be able to be immersed in a biological fluid, such as saliva, under the tongue. For example, the sensor can be about 1-2 mm sq.

In embodiments, the coating actively partitions a molecule, such as an electrochemically active molecule, from the sample. In further embodiments, the coating limits the partitioning of at least one molecule in the sample, wherein the molecule whose partitioning is limited is hydrophilic, lipophobic, or a combination thereof. For example, limiting the partitioning of molecules prevents biofouling of the sensor.

In embodiments, the electrochemically active molecule is hydrophobic, lipophilic, or both. A hydrophobic molecule, for example, repels or generally poorly mixes with water. A hydrophobic molecule, for example propofol, may fail to mix with water. A lipophilic molecule, for example, tends to combine with or dissolve in lipids or fats. A molecule, such as THC, can be both hydrophobic and lipophilic.

In embodiments, the molecule has a log $P_{O/W}$ value of less than about −10, about −10 to about −5, about −5 to about 0, about 0 to about 5, about 5 to about 10, about 10 to about 15, or greater than about 15. For example, the electrochemically active molecule, such as THC, has a log $P_{O/W}$ value of about 5.6. the log $P_{O/W}$ value represents the octanol water partition coefficient that is a log scale. For example, it is 10 to the power of 5.6, or ~870,000:1, for THC. In embodiments, the molecule can have a $P_{O/W}$ of zero, indicating the molecule is equally distributed between oil and water. In embodiments, the molecule can have a $P_{O/W}$ of negative values. This indicates that the drug is going to prefer to stay in the aqueous phase. Without being bound by theory, the higher the $P_{O/W}$ the more likely the drug will diffuse into the membrane permitting its measurement, In embodiments, the electrochemically active molecule has a partition coefficient of about 871,000:1 in a biological fluid. In further embodiments, the molecule has a partition coefficient of less than 871,000:1 in a biological fluid. In other embodiments, the molecule has a partition coefficient of greater than 871,000:1 in a biological fluid.

In embodiments, the electrochemically active molecule comprises at least one molecule from a *Cannabis* plant, a metabolite thereof, or a combination of both. Non-limiting examples of such molecules comprise tetrahydrocannabinolic acid (THCA), a metabolite of THCA, a prodrug of THCA, or a combination thereof. Additional non-limiting examples comprise $\Delta^9$-tetrahydrocannabinol (THC), 11-hydroxy-$\Delta^9$-tetrahydrocannabinol (11-hydroxy-THC), and 11-nor-9-carboxy-tetrahydrocannabinol (11-nor-9-carboxy-THC).

In embodiments, the electrochemically active molecule comprises the general structure:

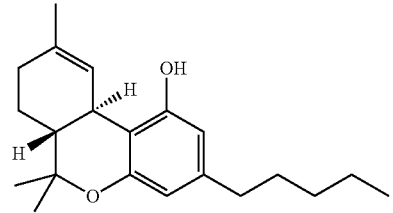 [SMILES: CCCCCc1cc(O)c2c(c1)OC(C)(C)[C@@H]1CCC(C)=C[C@@H]21]

In embodiments, the electrochemically active molecule comprises an anesthetic, such as propofol (see FIG. 3). In embodiments, the electrochemically active molecule comprises morphine, or illicit drugs. Non-limiting examples of illicit drugs comprise heroin, cocaine, acid, and LSD.

In embodiments, the sensor comprises a sublingual sensor, or a sensor manufactured to be placed under the tongue. In further embodiments, the sensor is manufactured to be placed in the mouth, such as an oral sensor, or against the skin, such as a temporal sensor.

In embodiments, the sample comprises an unprocessed sample, such as a sample of a subject at the point of contact. Unprocessed samples comprise those that are not subject to intermediate processing steps. For example, the samples are not subject to manipulation or modification prior to being contacted by the sensor as described herein.

Embodiments as described herein comprise a method for detecting, measuring, quantifying, distinguishing, or identifying at least one molecule in a sample of a subject, the method comprising contacting the sample with the electrochemical, voltammetric sensor of the devices described herein for a period of time sufficient to generate a voltammetric signal, wherein the voltammetric signal correlates to the presence of the molecule in the sample, the identity of the molecule in the sample, the concentration or amount of the molecule in the sample, or a combination thereof.

In embodiments, the method comprises contacting the sample with the electrochemical, voltammetric sensor of embodiments as described herein for a period of time sufficient to generate a voltammetric signal, wherein the voltammetric signal correlates to the identification of the molecule in the sample.

In embodiments, the period of time comprises less than about 60, about 30, about 15, about 10, about 5, about 1 minute(s). In embodiments, the period of time comprises about 5, about 10, about 15, about 30, about 45, about 60 seconds.

In embodiments, the method further comprises identifying a subject who has used drugs within a prior period of time. Further embodiments comprise identifying a subject who has used drugs within about 1 hour, 1 day, 1 week, or 1 month.

Embodiments comprise a method for determining if a subject is impaired. For example, embodiments comprise contacting a sample of the subject with the electrochemical, voltammetric sensor of embodiments as described herein for a period of time sufficient to generate a voltammetric signal, wherein the voltammetric signal correlates to the presence, amount, identification, or combination thereof of a molecule in the sample of the subject, and wherein the presence, amount, identification, or combination thereof of a molecule is indicative of impairment of the subject.

In embodiments as described herein, the presence, amount, identification of an electrochemically active molecule (such as THC, propofol, or combination thereof), corresponds to a predetermined limit, molecule type, or combination thereof.

Embodiments comprise an apparatus for controlling the operation of a vehicle. For example, embodiments comprise a sensing unit comprising the electrochemical, voltammetric sensor of embodiments as described herein, wherein a voltammetric signal is generated by the presence, amount, identification, or combination thereof of the electrochemically active molecule in the sample of the subject; and a controlling unit in communication with the sensing unit, wherein the controlling unit controls at least one vehicle operation in response to the voltammetric signal received by the sensing unit from the sensor.

Embodiments comprise a method for preventing operation of a vehicle by a subject under the influence of an electrochemically active molecule. For example, embodiments comprise detecting, via the electrochemical, voltammetric sensor of embodiments as described herein, the presence, amount, identity, or combination thereof, of the molecule in a sample of the subject; signaling, by the sensor, a controlling unit configured to control at least one vehicle operation; and controlling, by the controlling unit, the at least one vehicle operation so as to control operation of the vehicle. Further embodiments comprise signaling by the sensor when the sensor detects the presence, amount, identity, or combination thereof, of the molecule in the sample over a predetermined limit. In embodiments, controlling comprises preventing, via the controlling unit, activation of the at least operation of the vehicle. For example, operation of the vehicle comprises an ignition system, a transmission system, a fuel system, or a combination thereof.

Other objects and advantages of this invention will become readily apparent from the ensuing description.

DETAILED DESCRIPTION OF THE INVENTION

Figure 1:
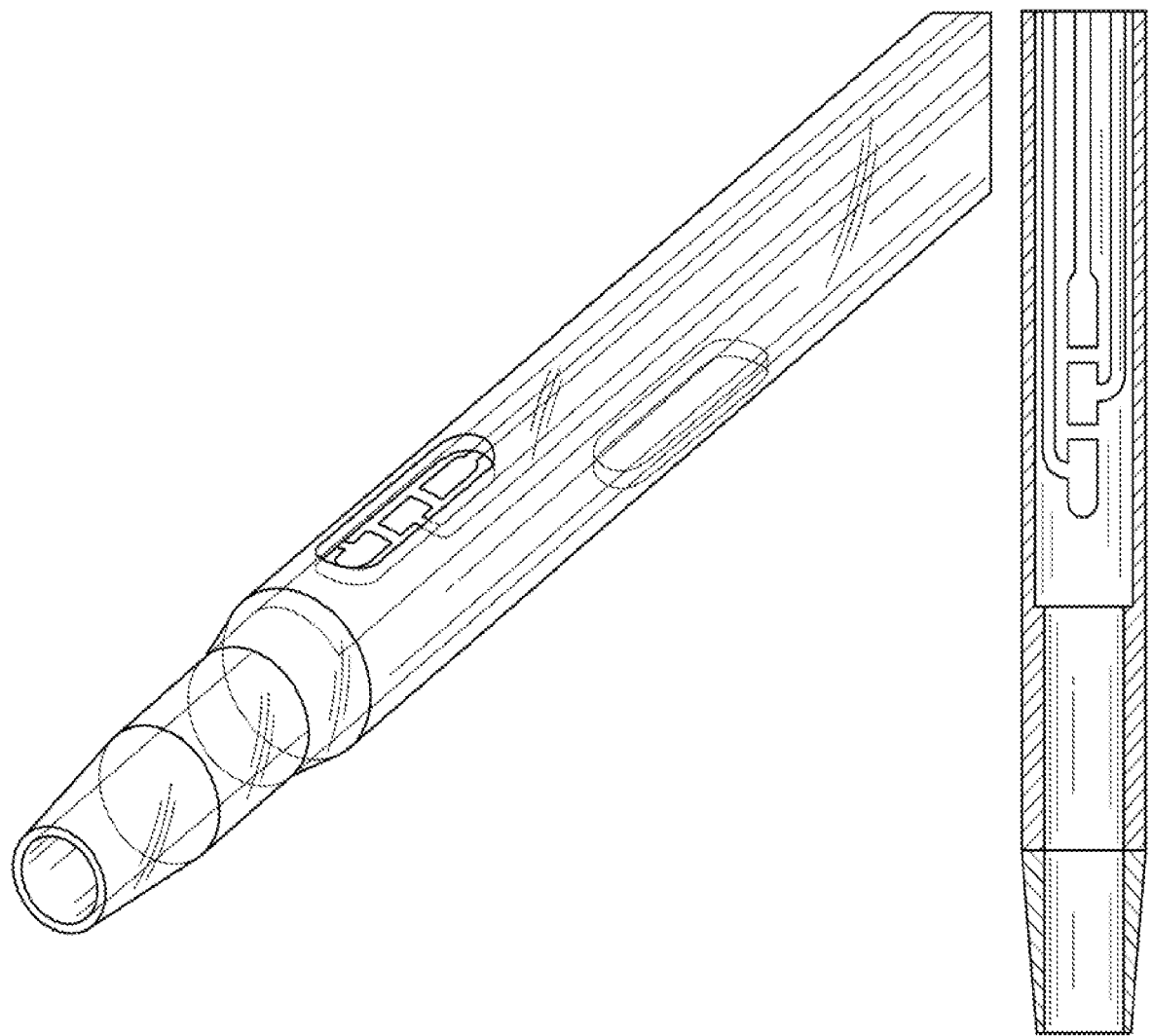
FIG. 1 shows CADs of prototype sublingual EC biosensors for the detection and quantification of THC and its metabolites in saliva.

The present invention is directed to non-invasive devices and methods to detect, measure, identify, or differentiate electrochemically active molecules, such as Tetrahydrocannabinol or metabolites thereof (see FIG. 5) in a fluid sample obtained from a subject. The user can use such non-invasive devices and methods at the point-of-contact with the subject, such as on the side of the road or in an automobile.

Detailed descriptions of one or more preferred embodiments are provided herein. It is to be understood, however, that the present invention can be embodied in various forms. Therefore, specific details disclosed herein are not to be interpreted as limiting, but rather as a basis for the claims and as a representative basis for teaching one skilled in the art to employ the present invention in any appropriate manner.

Abbreviations and Definitions

The singular forms "a", "an" and "the" include plural reference unless the context clearly dictates otherwise. The use of the word "a" or "an" when used in conjunction with the term "comprising" in the claims and/or the specification may mean "one," but it is also consistent with the meaning of "one or more," "at least one," and "one or more than one."

Wherever any of the phrases "for example," "such as," "including" and the like are used herein, the phrase "and without limitation" is understood to follow unless explicitly stated otherwise. Similarly "an example," "exemplary" and the like are understood to be nonlimiting.

The term "substantially" allows for deviations from the descriptor that do not negatively impact the intended purpose. Descriptive terms are understood to be modified by the term "substantially" even if the word "substantially" is not explicitly recited.

The terms "comprising" and "including" and "having" and "involving" (and similarly "comprises", "includes," "has," and "involves") and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a process involving steps a, b, and c" means that the process includes at least steps a, b and c.

Wherever the terms "a" or "an" are used, "one or more" is understood, unless such interpretation is nonsensical in context.

As used herein the term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

As used herein, the term "real-time" is intended to mean a response that is carried out within less than about a minute, preferably less than about 20 or 10 seconds, and most preferably within about 1 to about 5 seconds following a detection event.

Electrochemically Active Molecules

The present invention relates to devices and methods for measuring, identifying, and/or detecting the presence of one or more electrochemically active molecules in a fluid sample. Electrochemically active molecules can refer to those molecules that exchange electrons with other molecules. As described herein, the molecule that partitions into the coating of the sensor as described herein is oxidized, losing electrons and becoming more positively charged. Oxidation of the analyte provides the signal for the sensor of embodiments as described herein. In embodiments, the electrochemically active molecule can be said to "spontaneously partition" into coating of the sensor as a result of the molecule's chemical properties, such as its hydrophobicity and or lipophilicity.

Electrochemically active molecules that can be measured, identified, and/or detected by the present invention comprise those that are hydrophobic, lipophilic, or both. It is understood that hydrophobicity, lipophilicity or both can determined by methods known in the art, such as by Log P or Log D.

It is understood that hydrophobicity can be measured by Log P, which is the partition coefficient of a molecule between an aqueous and lipophilic phase. For example Log P(o/w) is commonly used, wherein O is octanol and W is water. Low hydrophilicity (and thus high hydrophobicity and high lipophilicity) is indicated by high log P values. In embodiment, the electrochemically active molecule can have a Log P of below 0, 0-1, 1-3, 3-5, or above 5. Preferably, the electrochemical molecule can have a Log P of 3-5, and more preferably, above 5. For example, the molecule can have a log $P_{O/W}$ value of about 5.6. The partition coefficient Log P is a constant for the molecule under its neutral form. The distribution coefficient Log D takes into account all neutral and charged forms of the molecule and, because the charged forms hardly enter the octanol phase, this distribution varies with pH.

Also, it is understood that hydrophobicity can be measured by a compound's partition coefficient, and for example, the molecule can have a partition coefficient of about 871,000:1 in a biological fluid.

It is understood that the invention can measure, identify, or detect any number of electrochemically active molecules, so long as the molecules are able to partition into the membrane of the sensor and generate a voltammetric such. As described herein, such molecules are generally hydrophobic and/or lipophilic.

Whether a molecule partitions into the coating of the sensor and generates an electrochemical voltammetric signal must be determined empirically, and cannot be determined by analysis of the structure of the compound alone. Non-limiting examples of electrochemically active molecules that can be measured, identified, and/or detected by the present invention comprise those compounds isolated from plants of the genus *Cannabis*, a genus of flowering plant in the family Cannabaceae. More than 450 compounds are unique to the *Cannabis* plant, including cannabinoids (such as THC, CBD, CBC, THCV, CBG, and CBN), with many more compounds widespread in the plant kingdom, such as terpenes. See, for example, Atakan, Zerrin. "*Cannabis, a complex plant: different compounds and different effects on individuals.*" *Therapeutic advances in psychopharmacology* 2.6 (2012): 241-254 and ElSohly, Mahmoud A., and Desmond Slade. "*Chemical constituents of marijuana: the complex mixture of natural cannabinoids.*" *Life sciences* 78.5 (2005): 539-548. the contents of each which are incorporated herein by reference in their entireties.

THC and many of its metabolites are highly lipophilic and essentially water-insoluble. Calculations of the n-octanol/water partition coefficient ($K_{OW}$) of THC at neutral pH vary between 6000 using shake-flask methodology and 9,440,000 by reverse-phase HPLC estimation. See Grotenhermen, F. *Pharmacokinetics and Pharmacodynamics of Cannabinoids; Clin Pharmacokinet* 2003; 42(4):327-360, which is incorporate by reference herein in its entirety. The wide range for aqueous solubility and $K_{OW}$, can be attributed to the difficulty of uniformly dissolving this essentially water-insoluble substance and accurately measuring small amounts of it.

Tetrahydrocannabinol (THC) can refer to a synthetic or semi-synthetic or a natural cannabinoid, including delta-9-tetrahydrocannabinol (Δ9-THC) and delta-8-tetrahydrocannabinol (Δ8-THC), mimicking the action of the natural neurotransmitter, anandamide, and responsible for the majority of the effects associated with binding to CB1 cannabinoid receptors in the brain.

11-Hydroxy-Δ9-tetrahydrocannabinol (11-OH-THC), or "11-hydroxy-THC", refers to the main active metabolite of THC, and is formed in the body after *cannabis* is consumed. Fresh *cannabis* contains tetrahydrocannabinolic acid (THCA), which is converted into THC after heating and then metabolized by the body into 11-hydroxy-THC and then into 11-nor-9-carboxy-THC. See FIG. 5. Both compounds can be glucuronidated and can be excreted into urine.

Cannabidiol (CBD) can refer to a non-psychotropic cannabinoid having little affinity for CB1 and CB2 receptors but acts as an indirect antagonist of cannabinoid agonists. CBD has been shown to play a role in preventing the short-term memory loss associated with THC.

Cannabinol (CBN) can refer to the primary product of THC degradation, there is usually little of it in a fresh plant. CBN content increases as THC degrades in storage, and with exposure to light and air. It is only mildly psychoactive. Its affinity to the CB2 receptor is higher than for the CB1 receptor.

Cannabigerol (CBG) refers to a non-psychoactive cannabinoid. CBG has been shown to promote apoptosis in cancer cells and inhibit tumor growth. It acts as an α2-adrenergic receptor agonist, 5-HT1A receptor antagonist, and CB1 receptor antagonist. It also binds to the CB2 receptor.

Tetrahydrocannabivarin (THCV) is prevalent in certain central Asian and southern African strains of *cannabis*. It is an antagonist of THC at CB1 receptors and attenuates the psychoactive effects of THC.

Cannabidivarin (CBDV) is usually a minor constituent of a cannabinoid profile, enhanced levels of CBDV have been reported in feral *cannabis* plants from the northwest Himalayas, and in hashish from Nepal.

Cannabichromene (CBC) is non-psychoactive and does not affect the psychoactivity of THC. CBC has shown antitumor effects in breast cancer xenoplants in an animal model. It is more common in tropical *cannabis* varieties.

It will be understood that other hydrophobic and/or lipophilic compounds can be measured or detected by the non-invasive device as described herein, including anesthetics (such as propofol), opioids (such as morphine, methadone, hydrocodone, oxycodone, heroin, opium), stimulants (such as cocaine, methamphetamine), and illicit drugs (such as lysergic acid diethylamide (LSD)).

Non-Invasive Device

The present invention relates to non-invasive devices, particularly non-invasive oral devices, configured for sensing, detecting, sampling, analyzing or monitoring of oral fluids, such as saliva, sputum and crevicular fluid, and various other body fluid samples, such as blood or urine. Additionally, the present invention relates to methods of sensing, detecting, sampling, monitoring or analyzing fluids by the sensing devices and related oral devices at the point of contact with a subject. More specifically, the present invention relates to devices and methods for non-invasive (or minimally invasive) sampling of body fluid samples, such as oral fluids or blood, of a subject at the point of contact with the subject.

The term "non-invasive" can refer to a procedure or device that does not alter a subject's tissue from its present state. For example, the skin does not need to be penetrated to measure an electrochemically active molecule using the non-invasive devices as described herein.

The term "fluid" or "fluid sample" can refer to a body fluid sample including, without limitation, oral fluids such as saliva, sputum, or crevicular fluid, or various other fluids, such as urine, lavage, tears, plasma, sweat or blood.

In embodiments, the sample is not processed (i.e., an unprocessed sample). In this context, an unprocessed sample can refer to a sample that has not undergone any purification procedures, and can include fluid samples obtained or collected at the point-of-contact with a subject. For example, unprocessed saliva comprises water, electrolytes (such as sodium, potassium, calcium, magnesium, bicarbonate, and phosphates), mucus, antibacterial compounds and proteins, such as enzymes, among other components.

In some embodiments, the fluid sample comprises an ex vivo fluid sample, such as a fluid sample that is outside of a subject. Non-limiting examples of ex vivo fluid samples comprise spit, lavage, tears, non-circulating blood (such as that from a wound). Ex vivo fluids can be obtained from a subject, such as manually obtained by a swab of the skin or of the oral mucosa. As desired, an embodiment of the device can be designed to first obtain and isolate a fluid sample from a subject, such as by a sampling unit, and then contact the isolated fluid sample with an electrochemical, voltammetric sensor as described herein so as to measure, detect, or identify an electrochemically active molecule.

In some embodiments, the fluid sample is not blood, plasma or serum. In some embodiments, the fluid sample is not circulating blood.

Figure 8:
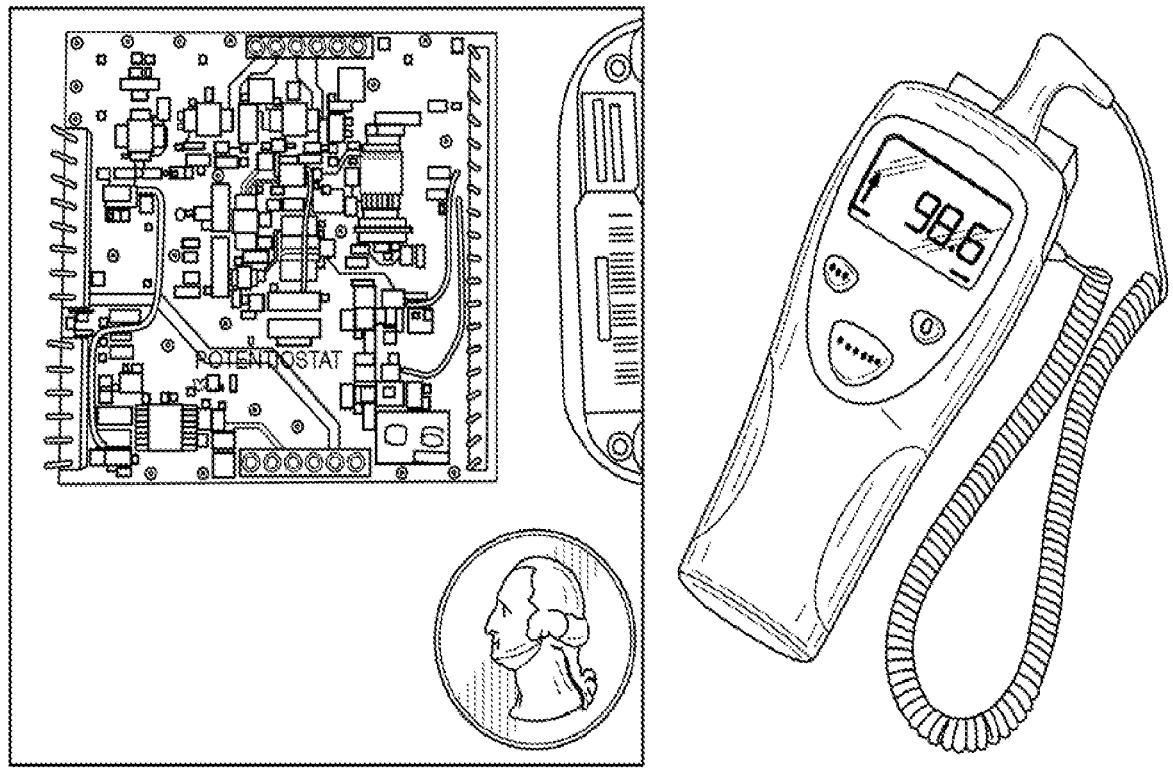
FIG. 8 shows prototype potentiostat (left) and design concept (right) for a hand held, sublingual THC detection device.
Figure 11:
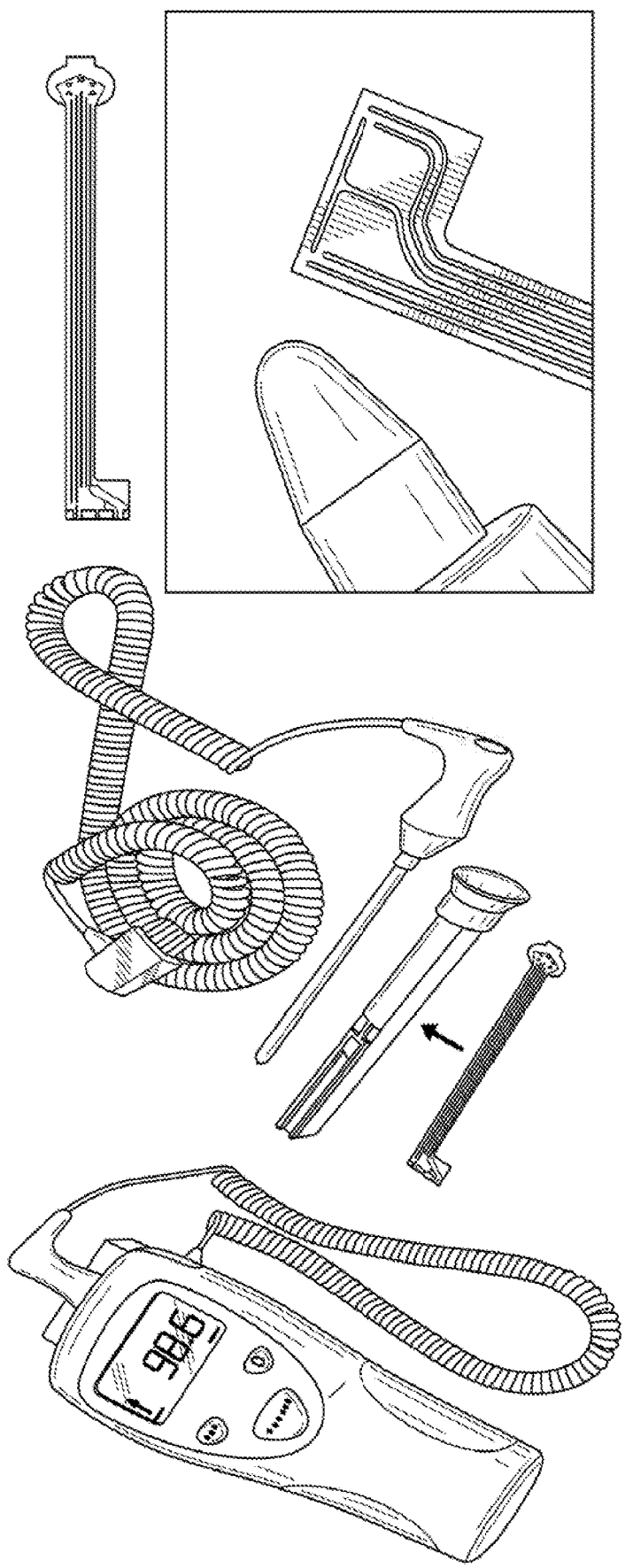
FIG. 11 shows POC device concept. Handheld device with readout (left), single-use biosensor for sublingual testing (middle), and circuit design with multiple, sensors for POC replicate testing (1,2, magnified right with pen tip). Capillary flow of saliva into a sealable chamber within the biosensor permits the non-invasive acquisition of a saliva sample at the time of testing for post-hoc validation by other methods.

As illustrated in FIG. 8 and FIG. 11, the non-invasive device can be designed as a portable device. As used herein, the term "portable" can refer to a device that can be carried or moved, such as with little or no effort. The term can also refer to a device that is not permanently affixed to a permanent structure and is of sufficiently low mass and bulk that it may be easily transported as part of a vehicle or transportation device. In a preferred embodiment, the device is handheld and is of a size and dimension that is analogous to a cell phone, oral thermometer or tablet computer.

While such non-invasive devices can be reusable, the non-invasive device can also be designed as a disposable device. The term "disposable" can refer to structures that are intended to be discarded after a single use or a few uses (i.e., they are not intended to be cleaned, laundered or otherwise restored and/or reused after use). Such structures may be recycled, composted or otherwise disposed of in an environmentally compatible manner. While the articles described herein are typically disposable, they may be designed to be cleaned, laundered, restored and/or reused many times. In certain embodiments, a portion of the device is disposable (such as the sensing unit, sampling unit, or portion thereof), while a different portion of the device is reusable (such as the controlling unit).

The non-invasive device can be designed to be placed in a body cavity, such as the oral cavity or anal cavity of a subject, so that the coating of the electrochemical voltammetric sensor is in contact with a subject's fluid sample. As illustrated in FIG. 1, the device can be designed to be placed in a subject's mouth, such as in the sublingual region or buccal region. Embodiments of the device can be sized according to the particular fluid and volume thereof to be sampled. For instance, when designed for sampling submandibular and sublingual saliva, the size of the sampling device should be minimized so as to be more easily manipulated to sample fluids from a subject's mouth. In other instances, when the sampling volume may be larger than that normally sampled by saliva glands, a larger device may be required.

In an embodiment, the non-invasive device comprises an electrochemical sensor as described herein. For example, the electrochemical sensor can comprise two or more electrodes and a coating that surrounds the two or more electrodes, where the coating is capable of selectively partitioning an electrochemically active drug, such as THC or a metabolite thereof (see FIG. 5), directly from the fluid sample, such as saliva, such that an oxidation/reduction current within the coating can be measured by the two or more electrodes. The coating also effectively partitions a biocompatible interface between the electrochemical sensor and a sample fluid, and/or prevents electrode fouling (because biological molecules in the fluid sample do not directly contact the electrodes in this embodiment).

In some embodiments, the coating of the sensor or a portion thereof is in direct contact with the fluid sample, thus allowing for the analyte(s) to partition into the coating so as to generate a voltammetric signal. For example, at least about 10%, 20%, 30%, 40%, 50%, 60%, 70%, 80%, 90% or 100% of the coating is in direct contact with the fluid sample.

It will be understood that the volume of the fluid sample must be sufficient to cover or immerse at least a portion of the coating sufficient to generate a voltammetric signal. For example, the volume of the fluid sample can comprise about 10 ml, 5 ml, 1 ml, 0.5 ml, 100 µl, 50 µl, 25 µl, 10 µl, 1 µl, or less.

Figure 12:
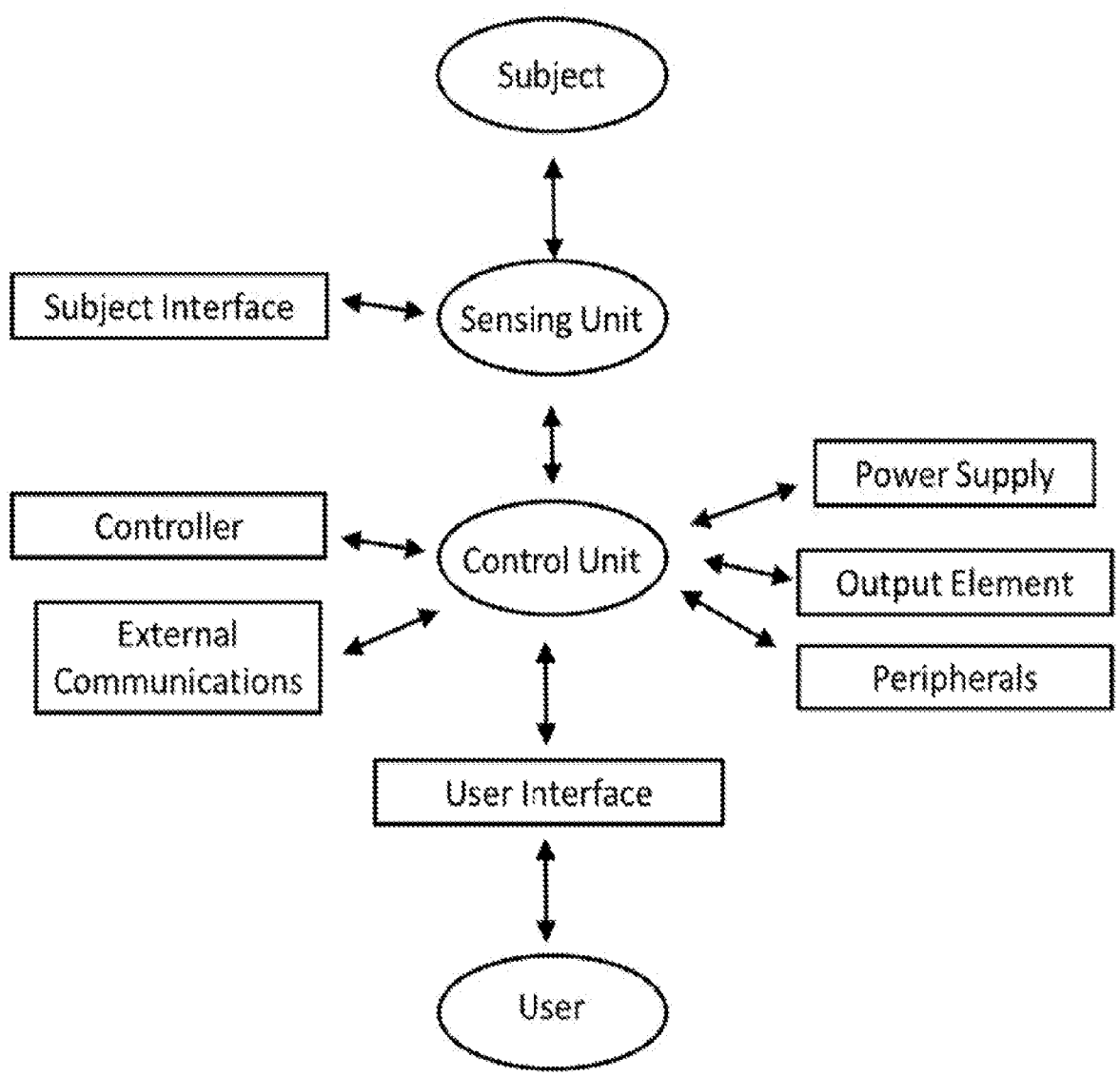
FIG. 12 shows a block diagram depicting one embodiment of the non-invasive device comprising a system that is equipped with a sensing unit and a control unit.

With reference to FIG. 12, a block diagram depicting one embodiment of the non-invasive device is illustrated comprising a system that is equipped with a sensing unit and a control unit.

The sensing unit can comprise electrochemical sensors as described herein as a component of the subject interface. For example, the subject interface includes an electrochemical sensor or sensor array of the present invention, which produces an output current from a reduction-oxidation (redox) reaction at electrochemical sensor in the presence of the electrochemically active molecule, such as THC. The amount of output current produced is in direct correlation to an amount of electrochemically active molecule detected during a measuring event (i.e., within a subject fluid sample). The output current from electrochemical sensor is coupled to a current/voltage detector which can be configured to convert the detected current output from electrochemical sensor into a corresponding calibrated value.

The control unit can include one or more components, such as a user interface, controller (such as a software controlled controller), peripherals, output element, power supply, and external communications. The controller may comprise one or more applications running on at least one processor. The controller may comprise one or more microcontrollers.

Using the sensor or sensor array of the present invention in combination with fluid samples containing known concentrations of an electrochemically active molecule, it is possible to generate empirical data that correlates the detected conditioned current/voltage levels with the molecule concentration. This empirical data can be used to form a model, which can be stored in memory.

The controller can include an input/output (I/O) card coupled through a data bus into a processor. The conditioned current at the output of current/voltage detector is provided to an analog to digital converter (ADC) of controller. The ADC converts the analog output of current/voltage detector to a corresponding digital value for processing by controller. The digital value of the detected current is provided to central processing unit (CPU)/processor. By way of example only, the ADC can be an 8-bit ADC, although other types of ADCs may also be used as known to those skilled in the art.

CPU/processor receives and processes the digital current from ADC. CPU/processor can be in the form of a single board computer which includes one or more microprocessors or CPUs. Controller may be conveniently implemented using one or more general purpose computer systems, microprocessors, digital signal processors, and microcontrollers, programmed according to the teachings described and illustrated herein. For example, CPU/processor can be an Intel Core Duo® processor provided by Intel Corporation of Santa Clara, Calif. Alternatively, CPU/processor may be a special purpose processor designed and fabricated to carry out various aspects of this invention. For example, CPU/processor may be an application specific integrated circuit (ASIC) chip.

CPU/processor is coupled to a memory that stores various settings, such as for the device. For example, memory stores one or more threshold values of the output current from electrochemical sensor, which threshold values represent the target range for the electrochemically active molecule concentration, i.e., minimum and maximum concentrations. The memory can be a random access memory (RAM) and/or read only memory (ROM), along with other conventional integrated circuits used on a single board computer as are well known to those of ordinary skill in the art. Alternatively or in addition, the memory may include a floppy disk, a hard disk, CD ROM, or other computer readable medium which is read from and/or written to by a magnetic, optical, or other reading and/or writing system that is coupled to one or more processors. The memory can include instructions written in a computer programming language or software package for carrying out one or more aspects of the present invention as described and illustrated herein, although some or all of the programmed instructions could be stored and/or executed elsewhere.

Controller can include an input/output (I/O) device (e.g., an I/O card) coupled to CPU/processor. The user interface (e.g., display with keypad), external communications, peripherals, patient interface, and drug delivery can be coupled to the controller via said I/O device. The I/O device includes a bi-directional port for communication to/from other computing and/or electronic devices via a link. The port can also be used for charging the device via power supply, which can be a battery. By way of example only, the port can be a Universal Synchronous Bus (USB) port, although other types of communication and input/output ports may also be used, as known to those skilled in the art.

The internal bus is designed to carry data, power and ground signals, as known to one skilled in the art. By way of example only, internal bus can be a Peripheral Component Interconnect (PCI) bus, although other types of local buses (e.g., Small Computer System Interface or "SCSI") may also be used, as known to those skilled in the art.

User interface can be a suitable display panel on which instructions and data are presented to a user in both textual and graphic format. In addition, display can include a touch screen also coupled to the I/O device for accepting input from a user (e.g., a medical professional). The display can display the concentration of the electrochemically active drug concentration based on the output current or voltage that is generated by the electrochemical sensor. Further, the display can be substituted by or used in conjunction with an audio device (e.g., a speaker, a buzzer, or a beeper alarm) controlled by CPU/processor to indicate whether the bioavailable drug concentration is too high or too low.

The controller receives power from a power supply. Power supply can be a battery or a direct pluggable outlet, such as to a port in a car or to a main power-line. Alternatively, power supply may be a switched mode power supply (SMPS) commonly used in computer systems, although other forms for powering controller using power supply may also be used, as known to those skilled in the art.

The controller preferably carries out a PID controller algorithm using the input from the electrochemical sensor. The PID controller involves three separate parameters: the Proportional, the Integral and Derivative values. The Proportional value determines the reaction to the sensed electrochemically active molecule concentration, the Integral value determines the reaction based on the average molecule concentration, and the Derivative value determines the reaction to the rate at which the molecule concentration has been changing. In the context of the present invention, any one of these parameters or the weighted sum of any two (or all three) of these parameters can be used to determine whether or not a subject is under the influence of a drug.

An output element can refer to any component that displays visual elements, such as those corresponding to the voltammetric signal, the presence of a molecule in a sample, the concentration of a molecule in a sample, the identification of a molecule in a sample, or a combination thereof. The visual elements can comprise, among others, bars, cursors, icons, images, and a string of characters that may be recognized and understood by a user as conveying one or more pieces of information. The output elements of an application are selected, scaled or organized based on the presentation descriptions of the application.

Electrochemical, Voltammetric Sensor

The sensor as described herein functions to detect, quantify, measure, and/or identify molecules in a fluid sample without biofouling by excluding those molecules which are not hydrophobic, not lipophilic, or a combination thereof, by virtue of their structure. Thus, the coating is able to selectively partition an electrochemically active molecule from a fluid sample. For example, the coating of the sensor uses the hydrophobic and lipophilic qualities of a molecule, such as THC or propofol, and also the hydrophobic properties of the coating itself to actively (i.e., spontaneously) partition the molecule from the fluid sample into the coating of the sensor. Thus the hydrophobic properties of the coating critical to the usefulness of the sensor.

One embodiment of the electrochemical sensor includes two or more electrodes, and a coating that surrounds the two or more electrodes.

The minimum number of electrodes used for each of these sensor designs is well known in the art. A voltammetric sensor can include, without limitation, one or more working electrodes in combination with a reference electrode, or one or more working electrodes in combination with a reference electrode and a counter electrode. In voltammetry, different potential programs can be applied to the working electrode, e.g., the potential can be varied over time (linear sweep voltammetry or cyclic voltammetry), potential can also be constant (chronoamperometry) or applied as pulses with the same or changing amplitude (pulse voltammetric methods) to measure the current related to the analyte concentration with the membrane coated sensor. A chronoamperometric sensor typically utilizes one or more working electrodes in combination with a reference electrode and a counter electrode, and the potential applied to the working electrode is constant or is applied as short pulses to measure the current related to the oxidation or reduction of the analyte with the membrane coated sensor. Chronoamperometry typically yields a better signal to noise ratio in comparison to other amperometric techniques. A conductometric sensor can include two or four electrodes, which measure the impedance of the coating with the sample solution. A potentiometric cell can include two electrodes, in which the potential of the indicator electrode is measured at zero current. A coulometric sensor can include two or more electrodes and measures the charge related to the oxidation or reduction of the analyte in the membrane coating. The design and principles surrounding these types of electrochemical sensors are described in Bard and Falkner, *Electrochemical Methods*, John Wiley and Sons, New York (2001); and Toth et al., "Electrochemical Detection in liquid Flow Analytical Techniques: Characterization and Classification," *Pure Appl. Chem.* 76(6): 1119-1138 (2004), each of which is hereby incorporated by reference in its entirety.

Reference electrodes, counter or auxiliary electrodes, and the working electrode can be formed out of a suitable conductive material including, without limitation, carbon, silver, mercury, gold, platinum, palladium, ruthenium, rhodium or combinations thereof. The particular function and number of electrodes will depend upon the type of electrochemical sensor that is employed, and aspects of the present invention are not limited by specific formation(s) of the electrochemical sensor illustrated below. At least the working electrode is covered by the coating.

The coating is capable of selectively partitioning an electrochemically active drug directly from the sample such that an oxidation/reduction current within the coating can be measured by the two or more electrodes. The coating also effectively partitions a biocompatible interface between the electrochemical sensor and a sample fluid, and/or prevents electrode fouling (because biological molecules in the fluid sample do not directly contact the electrodes in this embodiment).

The properties of the coating, such as its water-immiscible properties, limits the partitioning of hydrophilic molecules from the sample into the coating. This property prevents electrode fouling and enhances selectivity of the sensor.

Embodiments comprise a microelectrode sensor that comprises a reference electrode, a counter electrode and a working electrode, each of which have at least one end surrounded with a coating through which one or more electrochemically active molecules can be partitioned. In embodiments, the entire electrode is surrounded with a coating as described herein. The electrodes are housed in a glass capillary, the end of which has been removed to expose the electrodes. Alternatively, coating may cover or surround more than the tip of reference electrode, counter electrode and working electrode, for example, the whole of electrochemical sensor could be embedded in the coating material.

The coating comprises a structural component, a water immiscible organic solvent, and a charge transfer component. The coating may optionally comprise one or more further additives including, without limitation, a membrane resistance controlling component and a biocompatibility enhancing component.

Any suitable structural component can be utilized in the coating. The structural component can be polymeric or non-polymeric. Exemplary structural components include, without limitation, porous carbon materials as well as polymeric materials selected from the group of polyvinylchloride (PVC), silicone rubber, polyurethane, (meth)acrylate polymer, polypyrrole, polythiophene, polyoctylthiophene, polyanaline, polyvinyl pyrrolidone, agarose, hydrogel, sol-gel materials, and combinations thereof. In certain embodiments, the structural component can form a relatively minor portion of the coating, and in other embodiments the structural component can form a major portion of the coating.

The structural component is present in an amount of about 5 to about 80 wt. percent of the total coating, more about 15 to about 70 wt. percent of total coating. In certain embodiments, the structural component is present in an amount of about 20 to 30 wt. percent of the total coating. In alternative embodiments, the structural component is present in an amount of about 30 to about 50 wt. percent of the total coating. In certain embodiments, the structural component can also serve as working electrode, e.g., porous three dimensional carbon materials.

Any suitable water immiscible organic solvent can be utilized in the coating. The organic solvent is responsible for assisting in the partitioning of the electrochemically active molecule from the fluid sample into the coating. Exemplary water immiscible organic solvents, without limitation, comprise 2-nitrophenyl octyl ether (o-NPOE), dioctyl sebacate (DOS), bis(2-ethylhexyl) sebacate, benzyl s-nitrophenyl ether, benzyl 2-nitrophenyl ether, bis(1-butilpentyl) adipate, bis(2-ethylhexyl) adipate, bis(2-ethylhexyl) phthalate, 1-chloronaphthalene, chloroparaffin, 1-octanol, 1-decanol, dibutyl phthalate, dibutil sebacate, dibutyl-dilaurate, dodecyl 2-nitrophenyl ether, and combinations thereof.

In certain embodiments the organic solvent can be a fluorinated liquid, e.g. without limitation perfluorooctane, perfluorononane, perfluoro(2-methyloctane), perfluorodecaline and combinations thereof. In certain embodiments where the structural component forms a minor portion of the coating, then the organic solvent can form a relatively major portion of the coating; and in other embodiments where the structural component form a major portion of the coating, then the organic solvent can form a relatively minor portion of the coating.

The organic solvent is present in an amount of about 5 to about 85 wt. percent of the total coating, more about 10 to about 70 wt. percent of total coating. In certain embodiments, the organic solvent is present in an amount of about 45 to about 55 wt. percent of the total coating. In one alternative embodiment, the structural component is present in an amount of about 30 to 45 wt. percent of the total coating. In another alternative embodiment, the structural component is present in an amount of about 55 to about 70 wt. percent of the total coating.

Any suitable charge transfer agent can be utilized in the coating. Exemplary charge transfer components include, without limitation, tetradecylammonium tetrakis(pentofluorophenyl)borate (TDATPFPB), tetrahexylammonium perchlorate, and combinations thereof.

Any suitable membrane resistance controlling agent can be utilized in the coating, when desired. Exemplary membrane resistance controlling agents comprise, without limitation, lipophilic electrolytes, tetradodecyl ammonium-tetrakis(4-chlorophenyl) borate (ETH500), bis(triphenylphoranylidene) ammonium tetrakis[3,5-bis(trifluoromethyl)phenyl]borate (BTPPATFPB), and combinations thereof.

The resistance decreasing component is an organic salt that is not soluble in water and includes both a lipophilic cation and a lipophilic anion. As used herein, an organic salt that is not soluble is one that is characterized by a log P value (indeed the logarithm of the membrane water partition coefficient) that is larger than 6.1 or log D value (membrane distribution coefficient) that is larger than 6.1 at the sample solution pH at which the analysis is performed. Considered in terms of the amount of organic salt lost from the membrane to an aqueous sample solution, for two hours of monitoring the amount of organic salt lost from the membrane is about 1% of the starting amount.

The lipophilic cation is an ammonium cation or phosphonium cation, more a quaternary ammonium cation or a tetraarylphosphonium cation. The quaternary ammonium cations are tetraalkylammonium cations where the alkyl groups are independently 1 to 48 carbon atoms, such as 4 to 24 carbon atoms.

Exemplary lipophilic cations include, without limitation, tetradodecylammonium, tetraphenylphosphonium, bis(triphenylphosphoranylidine) ammonium, dimethyldioctadecyl ammonium, hexadecyltrioctadecylammonium, methyltrioctadecylammonium, tetrahexadecylammonium, tetraoctadecylammonium, tetraoctylammonium, tridodecylmethylammonium, tris[(perfluorooctyl)propyl]ammonium, and combinations thereof.

The lipophilic anion is a borate, sulfonate, or a carborane, including halogenated or nonhalogenated carboranes.

Exemplary lipophilic anions include, without limitation, tetraphenylborate, tetrakis(pentafluorophenyl)borate, tetrakis(4-chlorophenyl)borate, tetrakis[3,5,bis(trifluoromethyl)phenyl]borate, tetrakis(4-fluorophenyl)borate, dinonylnaphthalene sulphonate, tetrakis[3,5-bis(perfluorohexyl)phenyl]borate, tetrakis(p-tolyl)borate, tetrakis(m-tolyl)borate, tetrakis(2,4-dimethyl)borate, tetrakis(3,5-dimethylphenyl)borate, closo-dodecacarborane, undecachlorinated carborane (UCC), hexabrominated carborane (HBC), undecaiodinated carborane (UIC), undecabromocarborane, and combinations thereof.

Thus, exemplary water insoluble organic salts of the invention include, without limitation: tetradodecylammonium tetrakis(pentafluorophenyl) borate (TDDATPFPhB), bis(triphenylphosphoranylidene)ammonium tetrakis[3,5,bis(trifluoromethyl)phenyl]borate (BTPPATFPhB), tetradodecylammonium tetrakis(4-chlorophenyl)borate, tris[(perfluorooctyl)propyl]ammonium tetrakis[3,5-bis(perfluorohexyl)phenyl]borate, tetraheptylammonium tetraphenylborate, tetradodecylammonium dinonylnaphthalene sulphonate, tetraphenylphosphonium tetraphenylborate, tetraphenylphosphonium tetrakis(pentafluorophenyl)borate, tetraphenylphosphonium tetra-p-tolylborate, tetraphenylphosphonium tetra-m-tolylborate, bis(triphenylphosphoranylidene)ammonium tetraphenylborate, bis(triphenylphosphoranylidene)ammonium tetrakis(pentafluorophenyl)borate, bis(triphenylphosphoranylidene)ammonium tetrakis(4-chlorophenyl)borate, bis(triphenylphosphoranylidene)ammonium tetrakis[3,5,bis(trifluoromethyl)phenyl]borate, bis(triphenylphosphoranylidene)ammonium tetrakis(4-fluorophenyl)borate, hexadecyltrioctadecylammonium tetraphenylborate, tetraoctadecylammonium tetraphenylborate, tetraoctadecylammonium tetrakis(4-chlorophenyl)borate, tetraoctadecylammonium tetraphenylborate, tetraoctadecylammonium tetrakis(4-chlorophenyl)borate, tetraoctadecylammonium tetrakis(4-fluorophenyl)borate, tetraoctylammonium tetraphenylborate, tetraoctylammonium tetrakis(pentafluorophenyl)borate, tetraoctylammonium tetrakis(4-chlorophenyl)borate, tetraoctylammonium tetrakis[3,5,bis(trifluoromethyl)phenyl]borate, tetraoctylammonium tetrakis(4-fluorophenyl)borate, tridodecylmethylammonium tetraphenylborate, tridodecylmethylammonium tetrakis(pentafluorophenyl)borate, tridodecylmethylammonium tetrakis(4-chlorophenyl)borate, tridodecylmethylammonium tetrakis[3,5,bis(trifluoromethyl)phenyl]borate, tridodecylmethylammonium tetrakis(4-fluorophenyl)borate, tridodecylmethylammonium dinonylnaphthalene sulphonate, dodecyltrimethylammonium dinonylnaphthalene sulphonate, tetrabutylammonium tetraphenylborate, tetrabutylammonium tetrakis(pentafluorophenyl)borate, tetrabutylammonium tetrakis(4-chlorophenyl)borate, tetrabutylammonium tetrakis(4-fluorophenyl)borate, tetrabutylammonium tetrakis[3,5,bis(trifluoromethyl)phenyl]borate, tetraphenylphosphonium tetraphenylborate, trimethylammonium undecabromocarborane (TMAUBC), and combinations thereof.

The resistance decreasing component is present in an amount of about 1 to about 30 wt. percent of the total coating, more about 5 to about 25 wt. percent of the total coating. In certain embodiments, the resistance decreasing component is present in an amount of about 5 to about 10 wt. percent of the total coating. In alternative embodiments, the resistance decreasing component is present in an amount of about 10 to about 20 wt. percent of the total coating. In a further embodiment, the resistance decreasing component is present in an amount of about 20 to about 25 wt. percent of the total coating.

Any suitable biocompatibility enhancing component can be utilized in the coating, when desired. Exemplary biocompatibility enhancing components include, without limitation, nitric-oxide releasing sol-gel materials, N-(6-aminohexyl) aminopropyltrimethoxysilane, balanced isobutyltrimethoxysilane diazeniumdiolate, and combinations thereof.

The coating may optionally contain one or more further additives including, without limitation, adhesion enhancing and biocompatibility enhancing component, as well as any additional agents that inhibit certain biological responses, such as anti-inflammatory agents, anti-coagulants, etc.

The ion exchange component is either (i) a cation exchanger that includes a hydrophilic cation and a lipophilic anion, or (ii) an anion exchanger that includes a lipophilic cation and a hydrophilic anion.

The hydrophilic cation of the cation exchanger can be any water soluble cation. Exemplary hydrophilic cations include, without limitation, those selected from the group of alkali metal (e.g., lithium, sodium, potassium) cations, alkaline earth metal (e.g., magnesium, calcium) cations, transition metal (e.g., manganese, iron, zinc) cations, and complex (e.g., ammonium) cations.

The lipophilic anion of the cation exchanger can be any of the water insoluble borates, sulfonates, and halogenated and nonhalogenated carboranes as identified above for the resistance decreasing component.

Exemplary cation exchangers include, without limitation, sodium or potassium tetrakis[3,5bis(trifluoromethyl)phenyl] borate (NaTFPhB or KTFPhB), sodium or potassium tetrakis[pentafluorophenyl]borate (NaTPFPhB or KTPFPhB), sodium or potassium tetrakis(4-chlorophenyl) borate (NaTpClPhB or KTpClPhB), sodium or potassium tetraphenylborate, sodium or potassium tetrakis(4-fluorophenyl)borate, sodium or potassium tetrakis(p-tolyl)borate, sodium or potassium tetrakis(m-tolyl)borate, sodium or potassium tetrakis(2,4-dimethyl)borate, sodium or potassium tetrakis(3,5-dimethylphenyl)borate, sodium or potassium tetrakis[3,5-bis(1,1,1,3,3,3-hexafluoro-2-methoxy-2-propyl)phenyl] borate, sodium or potassium tetrakis[3,5-bis(perfluorohexyl)phenyl]borate, sodium or potassium tetrakis[3,5bis(trifluoromethyl)phenyl]aluminate, sodium or potassium tetrakis[pentafluorophenyl]aluminate, sodium or potassium tetrakis(4-chlorophenyl)aluminate, sodium or potassium tetraphenylaluminate, sodium or potassium tetrakis(4-fluorophenyl)aluminate, sodium or potassium tetrakis (p-tolyl)aluminate, sodium or potassium tetrakis(m-tolyl) aluminate, sodium or potassium tetrakis(2,4-dimethyl) aluminate, sodium or potassium tetrakis(3,5-dimethylphenyl)aluminate, and combinations thereof.

The lipophilic cation of the anion exchanger can be any of the water insoluble cations identified above for the for the resistance decreasing component. Non-limiting examples comprise the quaternary ammonium cations, bis(triphenylphosphoranylidene) ammonium cations, tris[(perfluorooctyl)propyl]ammonium cations, and tetraarylphosphonium cations identified above.

The hydrophilic anion of the anion exchanger can be any water soluble anion. Exemplary anions include, without limitation, those selected from the group of halides (e.g., $F^-$, $Cl^-$, $Br^-$, $I^-$), $NO_3^-$, $SO_4^{2-}$, $SO_3^{2-}$, $HSO_3^-$, $CO_3^{2-}$, $HCO_3^-$, $HPO_4^{2-}$, $H_2PO_4^-$, and $ClO_4^-$.

Exemplary anion exchangers include, without limitation, a quaternary ammonium chlorides, bromides, or perchlorates, and bis(triphenylphosphoranylidene) ammonium chlorides or bromides.

The ion exchange component is present in an amount of about 0.001 to about 30 wt. percent of the total coating, about 0.5 to about 25 wt. percent of total coating, or about 0.5 to about 5 wt. percent. In certain embodiments, the ion exchange component is present in an amount of about 0.5 to about 10 wt. percent of the total coating. In alternative embodiments, the ion exchange component is present in an amount of about 10 to about 20 wt. percent of the total coating. In a further embodiment, the ion exchange component is present in an amount of about 20 to about 30 wt. percent of the total coating.

In certain embodiments of the present invention, the coating includes about 5 to about 80 wt. percent of the structural component, about 5 to about 85 wt. percent of the water immiscible solvent, about 5 to about 30 wt. percent of the resistance decreasing component, and about 0.001 to about 30 wt. percent of the ion exchange component.

In another embodiment of the present invention, the coating includes about 15 to about 70 wt. percent of the structural component, about 10 to about 70 wt. percent of the water immiscible solvent, about 5 to about 30 wt. percent of the resistance decreasing component, and about 0.5 to about 5 wt. percent of the ion exchange component.

In certain exemplary embodiments, the coating includes about 20 to about 30 wt. percent of PVC as the structural component; about 45 to about 55 wt. percent of o-NPOE, DOS, or 1-octanol as the water immiscible solvent; about 20 to about 25 wt. percent of TDDATPFPhB or BTPPATFPhB as the resistance decreasing component; and about 2 to about 4 wt. percent of NaTFPhB or KTPFPhB as the ion exchanger component.

Any suitable adhesion enhancing component can be utilized in the coating, when desired for preventing the formation of an aqueous layer between the coating and the working electrode surface or between the coating and the planar electrochemical cell surface.

Any suitable biocompatibility enhancing component can be utilized in the coating, when desired. Exemplary biocompatibility enhancing components include, without limitation, nitric-oxide releasing sol-gel materials, N-(6-aminohexyl) aminopropyltrimethoxysilane, balanced isobutyltrimethoxysilane diazeniumdiolate, and combinations thereof. These can be used in amounts up to about 5 wt. percent, for example between about 0.001 to about 3 wt. percent.

Any suitable anti-inflammatory agents can be utilized in the coating, when desired. These can be used in amounts up to about 5 wt. percent, for example between about 0.001 to about 3 wt. percent. These agents should not interfere with the electrochemical signal caused by partitioning of the drug into the coating.

Any suitable anti-coagulant agents can be utilized in the coating, when desired. These can be used in amounts up to about 5 wt. percent, for example between about 0.001 to about 3 wt. percent. These agents should not interfere with the electrochemical signal caused by partitioning of the drug into the coating.

The coating can be of any suitable dimension that affords effective partitioning while allowing for sufficient electrochemical signaling within coating. For example, and not by limitation, in certain embodiments the coating is less than about 200 m thick, for example less than about 100 µm thick. According to one embodiment, the coating is between about 1 to about 25 µm thick. According to another embodiment, the coating has a sub-micron thickness.

Application of the coating over the electrode can be carried out by first forming a mixture of the component ingredients, which are dissolved in a suitable solvent such as THF, and then applying the dissolved solution using any of a variety of means including, without limitation, spray-coating, spin-coating, dip-coating, roller-coating, blade-coating, etc. The particular choice of coating technique will depend on its compatibility with the structure of the electrochemical cell that forms part of the sensing device of the present invention. During and subsequent to application the solvent used to disperse the components is removed, leaving the coating applied to a surface of the electrode(s).

According to one embodiment, the coating is formed from a composition including about 15 to about 67 wt percent PVC, about 33 to about 85 wt percent o-NPOE, and about 0.001 to about 15 wt percent TDATPFPB.

Coating can be of a suitable dimension that affords effective partitioning while allowing for sufficient oxidation/reduction current within coating. For example, and not by limitation, coating is less than about 200 µm thick, for example less than about 100 µm thick. According to one embodiment, coating has a sub-micron thickness. According to another embodiment, coating is between about 1 to about 25 µm thick.

Reference electrode, counter electrode and working electrode can be formed out of a suitable conductive material including, without limitation, carbon, gold, platinum, palladium, ruthenium, rhodium or combinations thereof. In certain embodiments four electrodes can be present. Further, various aspects of the invention are not limited by specific arrangement and structure of reference electrode, counter electrode and working electrode, and one skilled in the art after reading this disclosure may devise other arrangements and structures. Exemplary electrode functions include, working electrode, auxiliary or counter electrode, and reference electrode. The particular function and number of electrodes will depend upon the type of electrochemical sensor that is employed, and aspects of the present invention are not limited by specific formation(s) of electrochemical sensor.

Exemplary sensor formats comprise, without limitation, voltammetric sensors, potentiometric sensors, conductometric sensors, and coulometric sensors. A voltammetric sensor can include, without limitation, one or more working electrodes in combination with a reference electrode, or one or more working electrodes in combination with a reference electrode and a counter electrode. In voltammetry, the potential applied to the working electrode is varied over time to measure the current through either the coating (i.e., for the coated sensor embodiment) or in the fluid sample (i.e., for the uncoated sensor array embodiment). A conductometric sensor can include two or four electrodes, which measure the impedance of either the coating or the fluid sample. A potentiometric cell can include two electrodes, in which the potential of the indicator electrode is measured at zero current. A coulometric sensor can include two or more electrodes. The design and principles surrounding these types of electrochemical sensors are described in Toth et al., "Electrochemical Detection in liquid Flow Analytical Techniques: Characterization and Classification," Pure Appl. Chem. 76(6):1119-1138 (2004), which is hereby incorporated by reference in its entirety.

Another embodiment of the electrochemical sensor includes two or more electrodes in an electrode array. One form of construction includes a plurality of working electrodes, which are used in series such that each working electrode is used, only once or twice. This has the benefit of providing a new working electrode during each sensing process, and therefore biofouling of a working electrode (via proteins and other biomolecules in the fluid sample) is immaterial. The sensor according to this embodiment may include one or both of an auxiliary or counter electrode, and a reference electrode.

Another form of construction includes a plurality of sensor arrays, where each array includes the two or more electrodes required for the sensing format of choice, e.g., one or more working electrodes in combination with a reference electrode and a counter electrode for voltammetry. Embodiments comprise a microfluidic device that comprises a microfluidic channel and a plurality of carbon nanofiber sensors in array within the channel. One or more sensor arrays can be provided in each of a plurality of microfluidic channels.

Carbon nanofibers are compatible with a large number of microfabrication techniques including lithographic processing, material lift-off techniques, wet and dry etching, and chemical/mechanical polishing. As such, standard microfabrication techniques may be employed to incorporate into functional nanoscale electroanalytical platforms. Single CNFs can be synthesized on electrical interconnects and implemented as electrochemical electrodes with individual addressability down to ~1-2 micron interfiber spacing (Arumugam et al., "Wafer-scale fabrication of patterned carbon nanofiber nanoelectrode arrays: A route for development of multiplexed, ultrasensitive disposable biosensors," Biosensors Bioelectronics 24(9): 2818-2824 (2009); Melechko et al., "Vertically aligned carbon nanofibers and related structures: Controlled synthesis and directed assembly," J. Appl. Phys. 97(4):041301 (2005), each of which is hereby incorporated by reference in its entirety). Alternatively, the carbon nanofiber array can be prepared on a flexible substrate and then introduced to the interconnect (Fletcher et al., "Transfer of Flexible Arrays of Vertically Aligned Carbon Nanofiber Electrodes to Temperature-Sensitive Substrates," Adv. Mat. 18(13):1689-1694 (2006), which is hereby incorporated by reference in its entirety). Moreover, fabrication techniques allow only the nanoscale tip of these fibers to be electrochemically active (Huang et al., "Microelectrode Arrays for Electrochemistry: Approaches to Fabrication," Small 5(7):776-788 (2009); Potje-Kamloth et al., "Electrochemically Prepared Insulation for Carbon Fiber Microelectrodes," Berichte der Bunsengesellschaft für Physikalische Chemie 93(12):1480-1485 (1989), each of which is hereby incorporated by reference in its entirety). Thus, the nanofiber serves both to elevate the electroanalytical measurement volume above the planar substrate and to electrically bridge between the nanoscale dimensions of the fiber tip and the microscale dimensions of the electrical interconnects of the substrate. The electroactive tips of these vertically-oriented devices enable electroanalytical probing of extremely small volumes (<500 zeptoliter). This enables both the quantification of electroactive species as well as the direct manipulation of the local environment (oxidation, reduction, pH variation, field application, thermal modulation). These CNF probes can also be integrated with an active matrix thin film transistor array to significantly improve functionality and significantly increase the number of electrochemically active probes (400 probes in a 20×20 array, 1 mm2 footprint). This adds significant parallelism, offering high device density, large dynamic driving range, high temporal and electrophysiological signal sensitivity, and simpler driving electronics.

In embodiments, the electrical circuitry can be formed on the SiO2 substrate of a bulk silicon wafer using standard procedures. Thereafter, the carbon nanofiber array can be prepared such that each nanofiber is in electrical contact with the appropriate interconnect (see, e.g., Arumugam et al., "Wafer-scale fabrication of patterned carbon nanofiber nanoelectrode arrays: A route for development of multiplexed, ultrasensitive disposable biosensors," Biosensors Bioelectronics 24(9): 2818-2824 (2009); Melechko et al., "Vertically aligned carbon nanofibers and related structures: Controlled synthesis and directed assembly," J. Appl. Phys. 97(4):041301 (2005), each of which is hereby incorporated by reference in its entirety). Thereafter, SU-8 photoresist can be applied to the SiO2 surface and the surface of the carbon nanofibers (with the exception of the very tip of each nanofiber) (Huang et al., "Microelectrode Arrays for Electrochemistry: Approaches to Fabrication," Small 5(7):776-788 (2009); Potje-Kamloth et al., "Electrochemically Prepared Insulation for Carbon Fiber Microelectrodes," Berichte der Bunsengesellschaft für Physikalische Chemie 93(12): 1480-1485 (1989), each of which is hereby incorporated by reference in its entirety). Finally, SU-8 material in bulk can be adhered to the applied SU-8 coating to form the microfluidic channel.

A further embodiment is a microfluidic sensor array that does not contain carbon nanofibers. This array includes (i) the one or more electrodes in communication with a microfluidic channel through which the fluid sample passes during the detection procedure. The one or more electrodes in each array can optionally be coated with the coating described above in connection with sensor. Regardless, the coated electrodes are positioned with their coating in communication with the microfluidic channel through which the fluid sample passes during the detection procedure.

In one embodiment, a microfluidic biosensor is formed using a polyimide insulation and three microelectrochemical grid array sensors in series in a microfluidic channel formed in a polydimethylsiloxane ("PDMS") block. Each array includes a reference electrode, counter electrode, and working electrode. The working electrodes are formed as micro-disc arrays with 5 micron diameter gold discs positioned 50 µm center-to-center in a hexagonal arrangement. The channel is provided with an inlet and outlet for moving the sample through the microchannel and across the sensor array.

In another embodiment a microfluidic biosensor with polyimide insulation utilizes individually addressable gold microband arrays (only the electrode at the center) as working electrodes. The widths of the individual bands are between 2 and 10 microns. A complete biosensor includes the microband array working electrode, reference electrode, and counter electrode in a microfluidic channel formed in a PDMS block. The working electrodes is in the form of 5 µm wide individually addressable bands that are spaced 100 µm center-to-center. The sensors can optionally be interconnected with a single lead wire. The channel is provided with an inlet and outlet for moving the sample through the microchannel and across the sensor array.

In a further embodiment, a microfluidic biosensor is formed with polyimide insulation and three interdigitated array electrochemical sensors in series in a microfluidic channel formed in a PDMS block. Each array includes a reference electrode, counter electrode, and working electrode. The working electrode is in the form of an interdigitated electrode array that includes 5 µm wide fingers and 5 µm wide gaps between the fingers. The channel is provided with an inlet and outlet for moving the sample through the microchannel and across the sensor array.

In embodiments, the array electrodes can have varying dimensions ranging between, e.g., about 1 to about 15 microns, or for example, about 2 to about 10 microns. The 2 micron disc arrays have been fabricated with 20 microns center to center distance, 5 micron disc arrays have been fabricated with 50 microns center to center distance, and 10 micron disc arrays have been fabricated with 100 microns center to center distance. The interdigitated electrodes have been fabricated with 2 microns, 5 microns and 10 micron fingers in combination with 2 microns, 5 microns and 10 micron gaps, respectively. Finally, individually addressable microband arrays have been fabricated with 2, 5 and 10 micron wide bands spaced 40, 100, and 200 microns apart.

Regardless of the array format, microfluidic devices can be fabricated from materials that are biocompatible and resistant to biofouling. Several existing materials, widely used for the fabrication of fluidic channels, can address these basic needs. Two categories can be distinguished among them: those based on glasses, such as glass, Pyrex, quartz, etc. (Ymeti et al., "Integration of Microfluidics with a Four-channel Integrated Optical Young Interferometer Immunosensor," Biosens. Bioelectron. 20:1417-1421 (2005), which is hereby incorporated by reference in its entirety); and those based on polymers such as polyimide, photoresist, SU-8 negative photoresist, PDMS, and silicone elastomer PDMS (McDonald et al., "Fabrication of Microfluidic Systems in poly(dimethylsiloxane)," Electrophoresis 21:27-40 (2000), which is hereby incorporated by reference in its entirety), liquid crystal polymer, Teflon, etc. While the glass materials have great chemical and mechanical resiliency, their high cost and delicate processing make them less frequently used for this kind of application. In contrast, polymers have gained wide acceptance as the materials of choice for fluidics applications. Moreover, structuring technologies involved in their use, such as bonding, molding, embossing, melt processing, and imprinting technologies, are now well developed (Mijatovic et al., "Technologies for Nanofluidic Systems: Top-down vs. Bottom-up—A Review," Lab on a Chip 5:492-500 (2005), which is hereby incorporated by reference in its entirety). An additional advantage of polymer-based microfluidic systems is that valves and pumps made with the same material are readily integrated (Unger et al., "Monolithic Microfabricated Valves and Pumps by Multilayer Soft Lithography," Science 288: 113-116 (2000), which is hereby incorporated by reference in its entirety).

PDMS and SU-8 resist are particularly well studied as raw materials for the construction of microfluidic systems. Their mechanical and chemical comportment are strongly disparate: SU-8 is stiffer (Blanco et al., "Microfluidic-optical Integrated CMOS Compatible Devices for Label-free Biochemical Sensing," J Micromechanics Microengineering 16:1006-1016 (2006), which is hereby incorporated by reference in its entirety) than PDMS, and so the structuring techniques of these two materials are different. PDMS is also subject to wall collapse, depending on the aspect ratios of the channels (Delamarche et al., "Stability of Molded polydimethylsiloxane," Adv. Materials 9:741-746 (1997), which is hereby incorporated by reference in its entirety). Their chemical properties are an important aspect for the wanted application. They both have a hydrophobic surface after polymerization, which can lead to an attachment of the proteins onto the PDMS walls, and can fill the channel in case of small cross-section. Both the surface of PDMS and of SU-8 can be treated with a surfactant or by plasma to become hydrophilic (Nordstrom et al., "Rendering SU-8 Hydrophilic to Facilitate use in Micro Channel Fabrication," J Micromechanics Microengineering 14:1614-1617 (2004), which is hereby incorporated by reference in its entirety). The composition of SU-8 can also be modified before its structuring to become hydrophilic after polymerization (Chen and Lee, "A Bonding Technique using Hydrophilic SU-8," J Micromechanics Microengineering 17:1978-1984 (2007), which is hereby incorporated by reference in its entirety). Fouling of the channel surface via nonspecific binding is a concern for any microfluidic application. Anecdotal evidence suggests that SU-8 is less prone to this, but it is important to note that chemical treatment methods are also available for improving the performance of PDMS (Lee and Voros, "An Aqueous-based Surface Modification of poly(dimethylsiloxane) with poly(ethylene glycol) to Prevent Biofouling," Langmuir 21:11957-11962 (2004), which is hereby incorporated by reference in its entirety).

As noted above, the electrochemical sensor or sensor array is intended to be in contact with a fluid sample, such as an oral fluid (e.g., saliva) or other fluid that is easily sampled (e.g., blood or urine). As such, during use, the electrochemical sensor is intended to be exposed to, and in direct contact with, the fluid sample. To facilitate exposure to the fluid sample, a fluid sample can be drawn, obtained, or isolated from the subject and then exposed ex vivo to the sensor or sensor array. Thus, the sensor or sensor array according to any embodiment described herein is suitable for ex vivo detection of drug concentration.

For example, capillary flow of the fluid, such as saliva, into a chamber within the biosensor permits the non-invasive acquisition of a saliva sample at the time of testing. Capillary flow can refer to liquid getting into a microstructure or microchannel due to surface tension, and is widely applied in systems that need to transfer fluids without external power, such as lab on a chip, for example.

Alternatively, during use, the sensor or sensor array can reside in a device, such as an oral device, that is retained in fluid communication with the fluid sample in vivo, such as in the oral cavity of a subject. This type of device, because it is in constant exposure to the fluid sample during use, comprises the electrochemical sensor having the coating over the electrodes as described above (which prevents biofouling of the working electrode during use) or a sensor array (containing a plurality of working electrodes) as described above.

Detecting an Electrochemically Active Molecule in a Sample

Decreasing crashes, injuries, and fatalities from impaired driving is a priority, especially as more states move toward legalizing medicinal and recreational use of marijuana. Determination that a drug (such as THC, propofol, or an opioid such as heroin) is present in the body of a suspected drug-impaired driver close-in-time to the driving event is a critical, unmet need for law enforcement.

From the foregoing, it should be appreciated that the present invention relates to a non-invasive device and method for electrochemical detection or identification of one or more of an electrochemically active molecule in a fluid sample. The methods comprises the steps of: exposing a fluid sample to an electrochemical sensor of the non-invasive device wherein the sensor comprises one or more electrodes and a coating that surrounds the one or more electrodes, which coating is capable of partitioning the electrochemically active molecule directly from the fluid sample; and detecting an oxidation/reduction current during said exposing, wherein the detected current relates to the concentration of the electrochemically active molecule in the fluid sample. In embodiments, the fluid sample is obtained or isolated from a subject, such as by a sampling unit, prior to exposing the fluid sample to an electrochemical sensor.

In embodiments, the electrochemical sensor is contacted with the fluid sample for a period of time sufficient to generate a voltammetric signal which correlates to the presence of the molecule in the sample, the identity of the molecule in the sample, the concentration of the molecule in the sample, or a combination thereof. It will be understood that the period of time depends on variables such as the application of embodiments as described herein, the context in which the testing is being performed, and the pharmacokinetics of a particular drug. For example, the period of time can comprise less than about 10 minutes, preferably less than about 5 minutes, more preferably less than about 1 minute.

Further, the invention relates to a method of distinguishing between two or more molecules using the non-invasive device. Distinguishing between two or more molecules using a point-of-contact, non-invasive device requires that the electrochemical signal of each electrochemically active molecule be empirically determined and validated, as the electrochemical signal cannot be determined by structural analysis alone.

Figure 5:
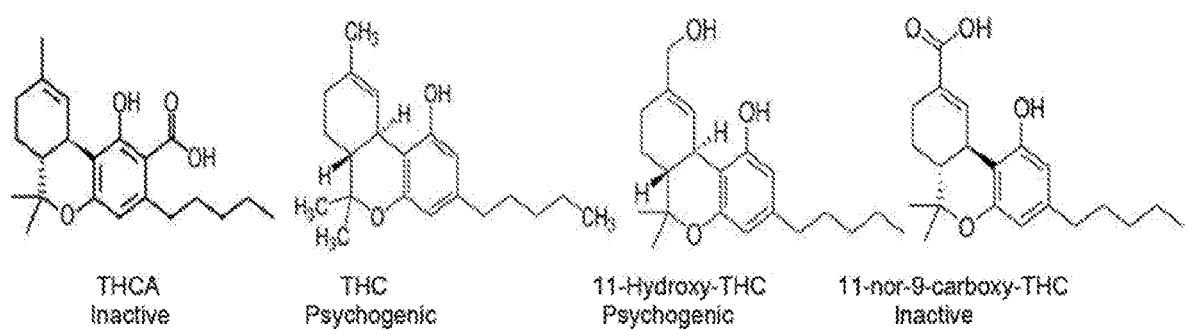
FIG. 5 shows THC and metabolites.

For example, a User may want to distinguish between psychogenic metabolites of THC and non-psychogenic metabolites of THC in a fluid sample using a non-invasive device as described herein. As illustrated in FIG. 5, fresh *cannabis* contains the compound tetrahydrocannabinolic acid (THCA), a precursor to the active drug, trans-Δ9-tetrahydrocannabinol (THC) that does not have any known psychoactive effects. Upon heating (such as by cooking or smoking), THCA is converted into THC (the primary psychogenic agent of *cannabis*) and metabolized by the body into 11-Hydroxy-Δ9-tetrahydrocannabinol (11-Hydroxy-THC). 11-Hydroxy-THC is also a psychoactive drug, is more potent than THC, and crosses the blood-brain barrier easily (Wall et al., 1983; Matsunaga et al., 1995; Watanabe et al., 1995). Peak THC concentrations are highest after smoking, conversely, 11-Hydroxy-THC/THC ratios are higher after oral administration due to its metabolism by the liver before entering the bloodstream. Smoked *cannabis*, goes directly from the lungs to the brain and is also briefly highly concentrated in the oral mucosa and saliva. 11-Hydroxy-THC is subsequently metabolized to 11-nor-9-carboxy-THC, the metabolite used to test for *cannabis* use in urine. It is not psychoactive and is not a measure of acute use. However, tests that can distinguish between 11-Hydroxy-THC and 11-nor-9-carboxy-THC, for example embodiments as described herein, can help to determine how recently *cannabis* was consumed.

Challenges of distinguishing between psychogenic and non-psychogenic metabolites of THC, for example, comprise detecting and optimization the electrochemical signal and response between psychogenic and non-psychogenic metabolites of THC as determined by empiric testing and observation; overlap of the electrochemical signal between psychogenic forms of the drug which can have different effects on cognition and metabolic time courses; and distinguishing between psychogenic and non-psychogenic forms of the drug which may share an electrochemical signal and responses, and thus may not accurately reflect the level of impairment or time course of recent use.

Electrochemically active molecules comprise those that exchange electrons with other molecules. As described herein, the molecule that actively partitions into the coating is oxidized, losing electrons and becoming more positively charged. Oxidation of the analyte provides the signal for the sensor of embodiments as described herein.

The sensors and devices described in U.S. application Ser. No. 13/124,036 (issued as U.S. Pat. No. 9,700,246) and U.S. application Ser. No. 14/404,674 describe sensors to be placed in vivo in a subject in a clinical setting to detect the concentration of drugs, such as an anesthetic, in circulating blood. More specifically, the sensors described in U.S. application Ser. No. 13/124,036 (issued as U.S. Pat. No. 9,700,246) and U.S. application Ser. No. 14/404,674 are designed to be placed inside the body, or underneath the skin, of a subject in a clinical setting to measure the concentration of drugs in circulating blood. Unlike these invasive devices, embodiments as described herein are suitable to be used in a non-invasive, non-clinical setting to measure the concentration of an electrochemically active molecule in an biological fluid. For example, the system has practical uses outside of the clinical setting, such as a point-of-contact (e.g., roadside) drug detection system or as an apparatus for controlling the operation of a vehicle. In such an embodiment, the biological fluid is an ex vivo biological fluid, such as one collected or obtained from a subject's mouth or on the surface of a subject's skin. In another example, the biological fluid is not blood, plasma or serum.

Electrochemical detection of drug concentration in circulating blood is different than electrochemical detection of an concentration of an electrochemically active molecule in non-circulating body fluid sample, such as saliva, in part due to the unique compositions of each fluid. Thus, electrochemical detection of the concentration of a molecule in non-circulating body fluid sample presents unique challenges relative to circulating blood.

For example, human saliva comprises approximately 99% water, whereas blood comprises approximately 80% water. Further, saliva comprises a unique composition of electrolytes, mucus, white blood cells, epithelial cells (from which DNA can be extracted), glycoproteins, enzymes (such as amylase and lipase), antimicrobial agents such as secretory IgA and lysozyme. Unlike blood, saliva contains enzymes that are essential in beginning the process of digestion of dietary starches and fats, and kill bacteria (such as salivary lactoperoxidase). Also, the electrolyte composition of saliva is different than that of blood. For example, the sodium concentration (2-21 mmol/L) and chloride concentration (5-40 mmol/L) are each lower than in blood plasma, while the concentrations of potassium (10-36 mmol/L) and bicarbonate (25 mmol/L) are each higher than in blood plasma. Further, red blood cells make up 40% of the blood volume, but there are no red blood cells in saliva. Still further, blood plasma is rich in albumin, whereas saliva has very little if any albumin.

Figure 13:
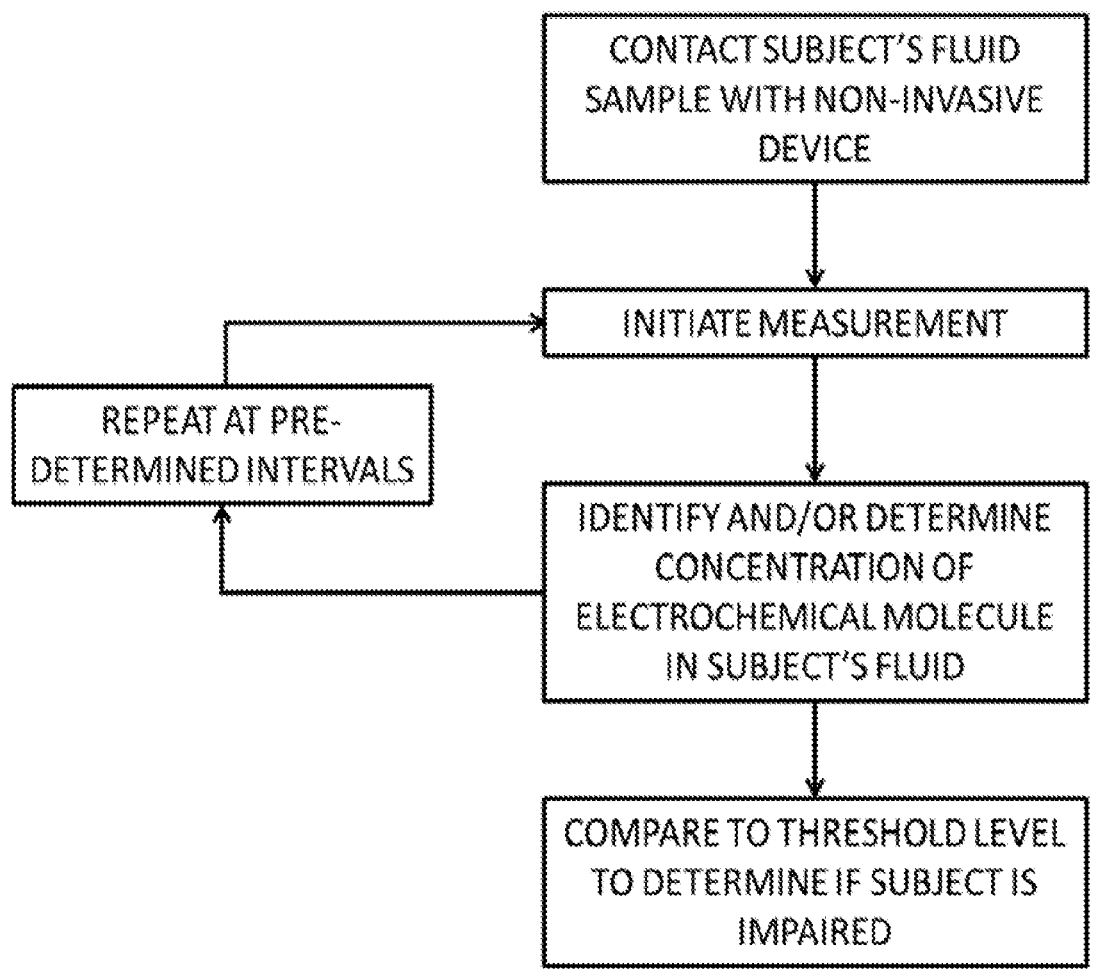
FIG. 13 shows a block diagram illustrating a method for determining if a subject is impaired using the non-invasive device.

Detecting an electrochemically active molecule, such as THC or heroin, in a fluid sample of a subject in a non-invasive manner has practical uses outside of the clinical setting. Referring to FIG. 13, a block diagram illustrating a method for determining if a subject is impaired using the non-invasive device is illustrated.

A subject's fluid, such as saliva, can be contacted with the sensing unit of the device (e.g., the electrochemical sensors) in either a non-invasive fashion (such as a sublingual sensor) or ex vivo (such as in a vessel or tube) for a period of time sufficient to generate a voltammeteric signal. In embodiments, the User can manually initiate the measurement of the electrochemically active molecule, such as by initiating the measurement using the control unit.

Mechanistically, the electrochemically active molecule, such as a hydrophobic analyte, actively (i.e., spontaneously) partitions into the hydrophobic coating surrounding the electrodes of the sensor as described herein, or a portion thereof, based on the properties of the analyte and the membrane itself (i.e., like attracts like). For example, the organic solvent in the coating, such as o-NPOE or DOS, assists in the partitioning of the electrochemically active molecule from the fluid sample. Together with the hydrophobic properties of the membrane, the partitioning of the analyte in embodiments of the sensor described herein is based on the chemical potential (the energy state) of the hydrophobic analyte, such as THC, in the aqueous solution and in the PVC membrane. Once partitioned into the coating, the hydrophobic analyte itself is oxidized. Oxidation of the hydrophobic analyte provides the signal for the sensor of embodiments as described herein, allowing for the identification of the electrochemical molecule and/or determination of the concentration of the electrochemical molecule.

Figure 7:
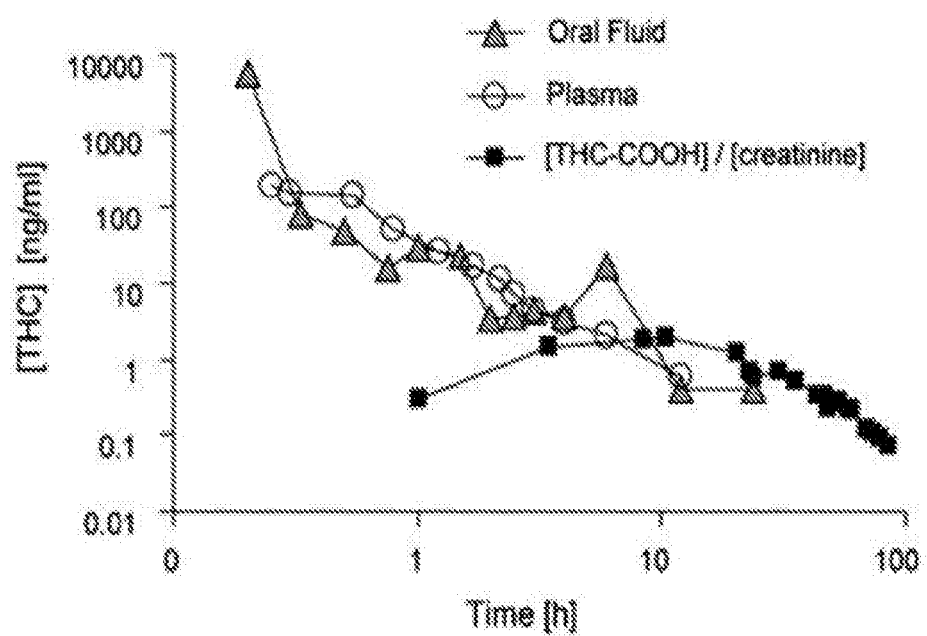
FIG. 7 shows correlation of THC in oral fluids and plasma vs. time, after inhalation. An initial spike in THC levels in saliva is seen immediately after smoke inhalation. After ~20 minutes there is direct correlation between the levels of THC measured in saliva and plasma.

Optionally, the measurement can be performed repeatedly, such as at predetermined intervals. It will be understood that use and timing of the measurement will be determined by variables such as the application of embodiments as described herein, the context in which the testing is being performed, and the pharmacokinetics of a particular drug. Referring to FIG. 7 for example, THC is highly concentrated in the saliva immediately after smoking and does not reflect blood levels until 20 to 30 minutes after smoking. Thus, the frequency of the replicate tests will depend upon the context in which the testing is being performed. It is generally desirable to repeat the detection procedure at least every 5 minutes, more preferably at least every 2 to 3 minutes. More frequent detection procedures, such as every 30 seconds or every 1 minute, can also be carried out.

Once the measurement(s) is obtained, the measurement of the electrochemically active molecule in the subject's fluid can be compared to a predetermined threshold level or to a control sample to determine if the subject is impaired. It is understood that the threshold is dependent on the particular electrochemical molecule measured.

The term "threshold", for example a THC threshold, can refer to a value derived from a plurality of biological samples, above which threshold is associated with an increased likelihood of being impaired.

The term "changed as compared to a control" sample or subject can refer to having a level of the analyte, such as THC, to be detected at a level that is statistically different than a sample from a normal state control sample. Determination of statistical significance is within the ability of those skilled in the art, e.g., the number of standard deviations from the mean that constitute a positive or negative result.

Many such uses of the non-invasive embodiments as described herein can contribute to public safety. For example, one such non-clinical application comprises identifying a subject who has used drugs within a prior period of time (such as within 1 hour, 1 day, 1 week, or 1 month of when the measurement is taken) or is presently under the influence of drugs. For example, non-invasive embodiments as described herein can be used in the workplace, such as with a pilot or one in control of heavy equipment. Additionally, non-invasive embodiments can be used in a school or by law enforcement offices. In such instances, the non-invasive device is manufactured to be used at the point of contact with the subject.

Further, non-invasive embodiments can be used for controlling the operation of a vehicle and/or preventing the operation of a vehicle. Methods and apparatus for controlling the operation of a vehicle and/or preventing the operation of a vehicle are generally known in the art (see U.S. Pat. No. 8,549,318, for example, which is incorporated herein by reference in its entirety). Using a non-invasive device comprising an electrochemical sensor as described herein, an exemplary method of controlling the operation of a vehicle comprises detecting the presence, amount, and/or identity of an electrochemically active molecule in a fluid sample of the subject by the sensor, and signaling a controlling unit to control at least one vehicle operation. Non-limiting examples of the vehicle operation controlled includes the ignition system, transmission system, fuel system or a combination thereof. Thus, embodiments can prevent the operation of or activation of the vehicle.

EXAMPLES

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

Example 1—Detection of THC Use in Drivers. "Point-of-Contact, Direct Assessment of THC and Psychotropic Metabolite Levels from Saliva Using a New, Point-of-Contact Electrochemical Biosensor"

Significance of the Problem

Decreasing crashes, injuries, and fatalities from impaired driving is a priority for the National Highway Traffic Safety Administration (NHTSA) as more states move toward legalizing medicinal and recreational use of marijuana. Determination that a drug (such as THC) is present in the body of a suspected drug-impaired driver close-in-time to the driving event is a critical, unmet need for law enforcement. Current tests for the presence of THC in blood or saliva require expensive laboratory equipment and processing of biological fluids, and thus cannot be performed at the roadside point of contact (POC). Testing in breath or saliva has not been validated and approved by the FDA, and current methods use indirect chromatographic methods that cannot distinguish different psychogenic metabolites. As marijuana is the drug of greatest interest, a device that could detect the presence of THC and its psychogenic metabolites at the POC would provide law enforcement officers and prosecutors with crucial information about potential impairment and also aid in decisions whether to pursue impaired driving charges by providing reliable evidence of quantitative drug levels in the driver. A portable device, similar to an alcohol breathalyzer testing device, would be an ideal tool for law enforcement, i.e., an innovative technology to determine the presence of THC in the body that is quick, easy to administer and minimally intrusive. Such a technology needs to be sensitive to and specific for THC levels (and its metabolites, such as its main active metabolite 11-hydroxy-THC), have accuracy similar to current mass spectroscopy and chromatography methods to minimize false positive and false negative tests, but also affordable and easily usable at the roadside by officers with reasonable training.

Technical Objectives

This project will validate the application of an innovative electrochemical biosensor technology for rapidly determining the concentration of THC and its psychoactive metabolites present in the saliva (FIG. 1). For example, one embodiment comprises a novel, point of care device designed as a sublingual sensor. Capillary flow of saliva into a sealable chamber within the biosensor permits the non-invasive acquisition of a saliva sample at the time of testing for post-hoc validation by other methods. This technology is a novel, real time method of drug detection in drivers under the influence of *cannabis*, close-in-time to the driving event.

Application of Electrochemical Biosensors to Measure Metabolites and Drugs

Figure 2:
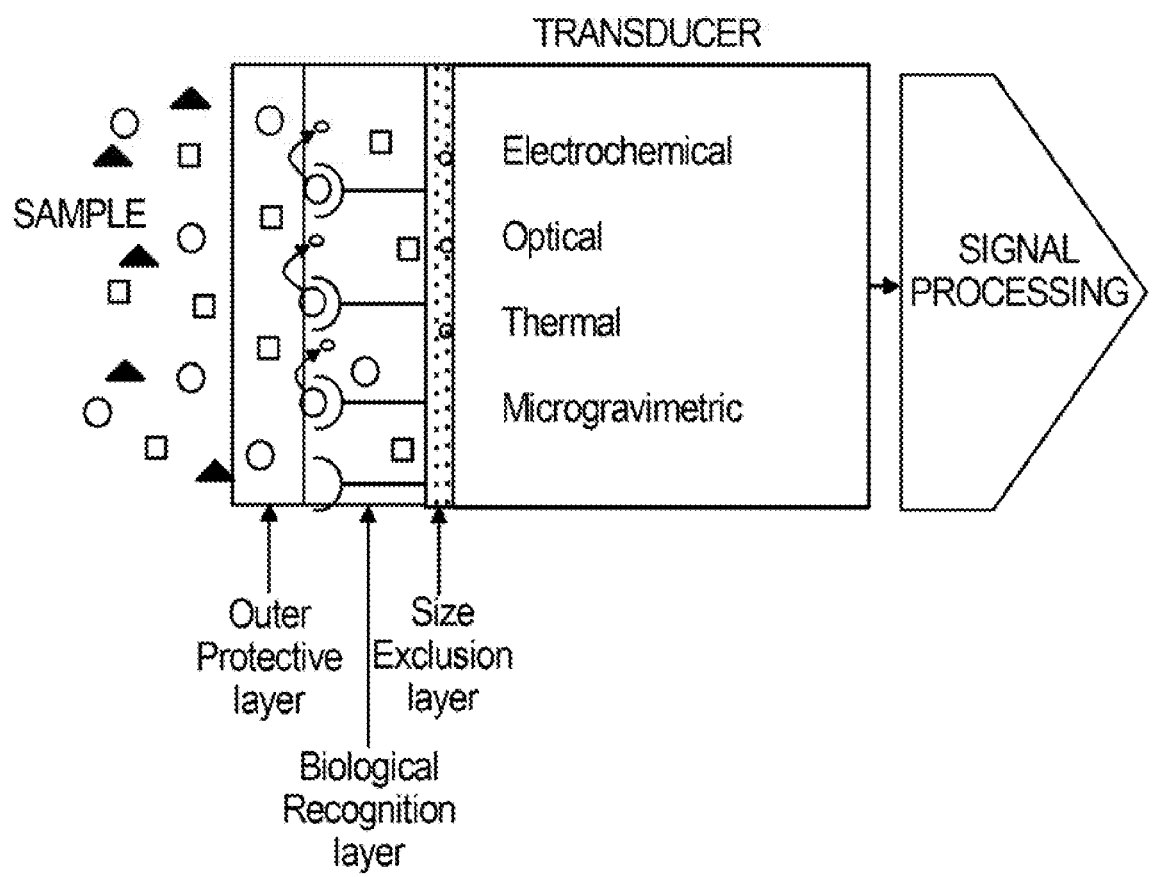
FIG. 2 shows electrochemical (EC) biosensors translate biological information into an electrical signal. ● primary analyte, • secondary analyte, ■ EC interferent, and ⋏ biological interferent.

Microfabricated chemical and biological sensors serve as an interface between biologic and electronic systems and function to transduce specific chemical information into electronic signals (FIG. 2). Current state of the art electrochemical (EC) sensors are in clinical use to measure the concentration of physiologically important ions (e.g. sodium, potassium, pH), small molecules (e.g., glucose, blood urea nitrogen, creatinine), and blood gases ($O_2$, $CO_2$) in the clinical laboratory and at the bedside using FDA-approved devices. The precision, accuracy, and sensitivity of these biological monitoring devices and their electronic output are well validated in medical practice. The reliability and accuracy of single use and monitoring devices are now equivalent to large clinical laboratory analyzers. As a direct result the costs have been significantly reduced and bedside testing of metabolites in blood has become widely adopted.

These methods are directly applicable to the detection and quantification of drug levels in blood and other biological fluids. A proof of concept and validation of accurate quantification of propofol (a highly lipophilic drug) directly in biological fluids and blood using a new electrochemical biosensor has been demonstrated. The results of this work include: 1) validation of biosensor performance in blood and other biological fluids, 2) accuracy equivalent to HPLC, 3) design and prototyping of a biosensor device for clinical use, and 4) driving electronics, software, and hardware prototypes. These results are presented in detail herein, such as in Section 4. Further, see U.S. Pat. No. 9,700,246; U.S. patent application Ser. No. 14/404,674, each of which are incorporated by reference herein in their entireties.

Technical Objectives required to demonstrate the feasibility of our biosensor technology to the development of a law enforcement device to detect and quantify THC have already been accomplished. This biosensor, as it currently performs, is capable of quantifying THC, thus embodying an accurate POC device capable of measuring THC levels in saliva, without requiring sample preparation. Described herein are the Technical Objectives required to demonstrate the biosensor use for the detection and quantification of THC, pharmacokinetic considerations, and medico-legal considerations for the application of this technology to identify drivers impaired by *cannabis* use.

Figure 3:
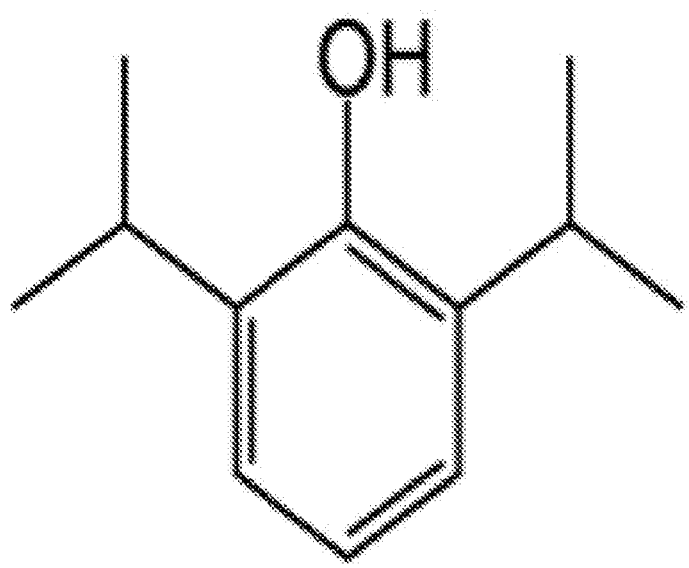
FIG. 3 shows the chemical structure of propofol, a highly lipophilic molecule.

The Electrochemistry of Propofol and the Application of a Biosensor for THC Detection The origins of this technology stem from the development of compositions and methods to directly measure the blood levels of propofol, a phenolic, lipophilic anesthetic drug, with the goal of real-time detection and monitoring in patients under anesthesia (FIG. 3). Previously, analytical methods for propofol, as with THC, were time consuming, required extraction from the blood, and used complex instrumentation, mass spectroscopy/liquid chromatography (MS/LC) and HPLC. Although highly quantitative, these methods are inadequate for the rapid quantification of drug levels at the bedside or for continuous monitoring.

The electrochemistry (EC) of phenol and its many derivatives has an extensive literature but previously, the EC of propofol was poorly understood and most EC methods were used in combination with HPLC [5-8]. The EC behavior of propofol was elucidated in a series of papers, and a biosensor developed and prototyped for use in the clinical detection and quantification of the drug in its use as a general anesthetic and sedative hypnotic. See Langmaier et al., *Electrochemical quantification of 2,6-diisopropylphenol (propofol). Anal. Chim. Acta* (2011); Kivlehan et al., *Toward Feedback-Controlled Anesthesia: Voltammetric Measurement of Propofol in Serum-Like Electrolyte Solutions. Analytical Chemistry* (2012); Rainey et al., *Toward Feedback Controlled Anesthesia: Automated Flow Analytical System for Electrochemical Monitoring of Propofol in Serum Solutions. Electroanalysis* (2014); Myers, et al. "*A Feedback Control Approach to Organic Drug Infusions Using Electrochemical Measurement.*" *IEEE Transactions on Biomedical Engineering* 63.3 (2016): 506-511, each of which are incorporated herein by reference in their entireties. Prior work in this field (presented in detail herein, such as in Section 4), describes the approach to the EC detection of THC; 1) it has a very high partition coefficient, 2) it is rapidly delivered to the brain to assert its psychogenic/neurologic effects, 3) it is rapidly metabolized by cytochrome P450 enzymes in the liver, and 4) it has a detectable electrochemical signal. The usefulness of EC methods to detect and quantify a specific compound is determined experimentally, and THC has been recently shown to demonstrate quantifiable electrochemical behavior. The utility of EC methods to detect and quantify a specific compound is not based on its structure alone, rather, it is determined experimentally, the results depending upon the chemical structure, the solute, the method applied, and the type of electrode used.

Technical Objective 1: Detection of THC by EC Methods
Electrochemical Detection of THC Current immunoassays for THC require expensive laboratory equipment, are inhibited by other drugs, and have a limited dynamic range compared with the chromatography. HPLC/MS/LC methods are accurate but the THC must first be extracted from biological fluids and thus is not translatable to roadside use. The successful application of an EC method for the detection and quantification of THC and its metabolites requires that the drug be electrochemically active, and thus able to generate a dose-dependent voltammetric signal. The utility of EC methods to detect and quantify a specific compound is not based on its structure alone, rather, it is determined experimentally, the results depending upon the chemical structure, the solute, the method applied, and the type of electrode used.

Figure 4A:
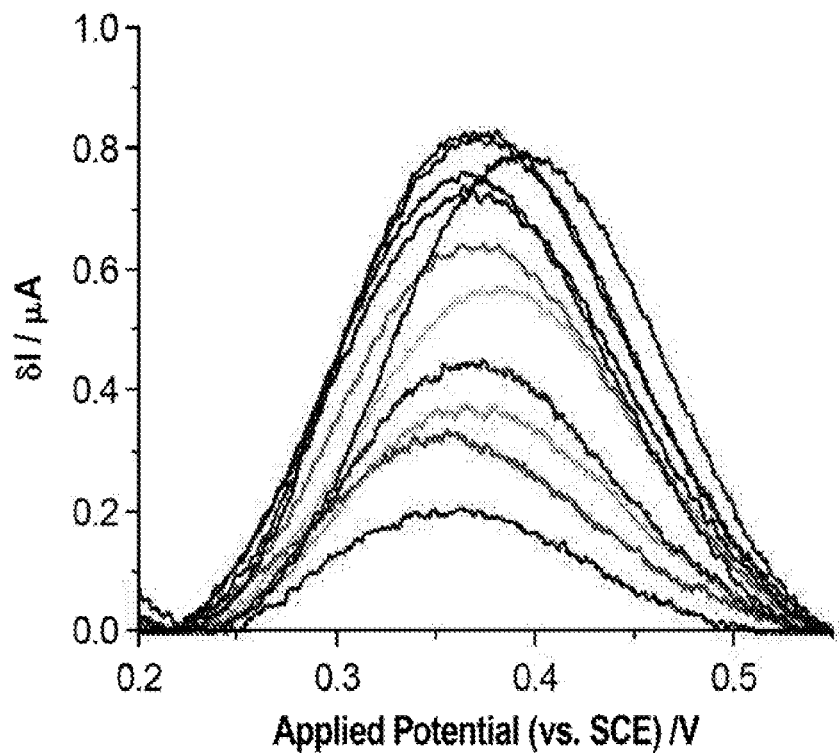
FIG. 4 shows a) square wave voltammograms for the oxidation of THC, seen at ca. +0.37V on the graphite/mineral oil paste electrode in synthetic saliva/BBS solutions that contained 0.10-16 µM THC; and b) the increase of the peak current with increasing THC concentration with the correlation line through the linear range (red line, $R2=0.99$) from Nissim, 2015.
Figure 4B:
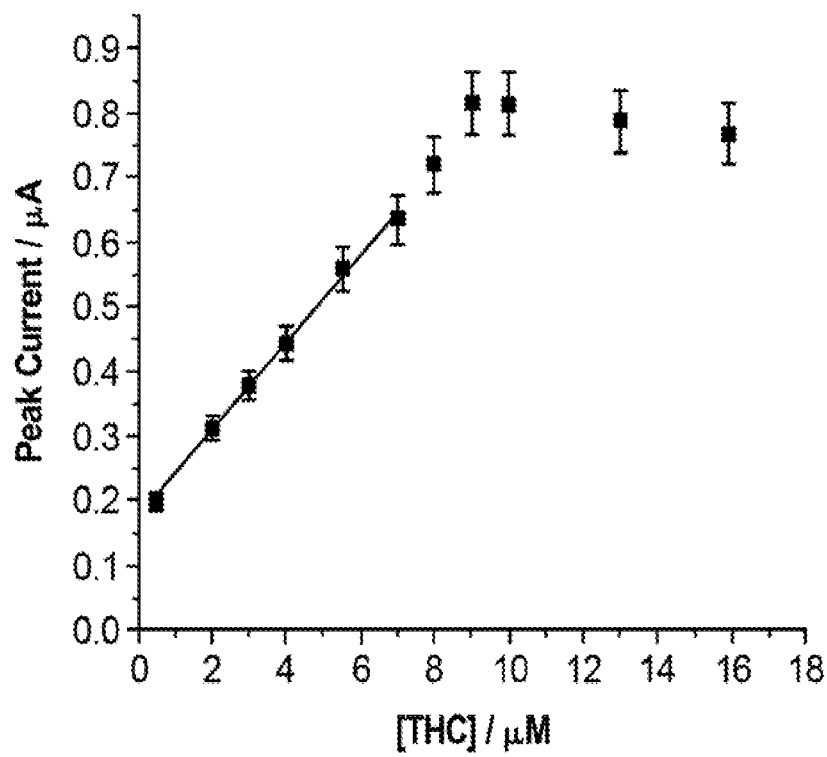

The electrochemistry of $\Delta^9$-THC has been reported using several methods, by absorptive striping voltammetry at a carbon paste electrode [Nissim, 2015, see FIG. 4], by square wave voltammetry at a glassy carbon electrode and at a paraffin-graphite electrode. In all cases, pre-concentration of $\Delta^9$-THC onto the electrode was used to maximize sensitivity (Nissim 2015; Balbino et al., 2014; Novak et al. 2013). The use of EC methods to detect THC has been shown at the level of 25-50 ng/mL $\Delta^9$-THC in undiluted saliva (Wanklyn, et al., 2016). Thus, the EC methods to detect THC in saliva at physiologically relevant levels have been established in the peer-reviewed literature.

The novel aspect of embodiments of the invention is that its lipophilic coating permits the diffusion of organic molecules away from the saliva to the detector surface (thus pre-conditioning is not required). See U.S. Pat. No. 9,700, 246; U.S. patent application Ser. No. 14/404,674, each of which are incorporated by reference herein in their entireties. Like propofol, THC is a highly lipophilic drug ($P_{o/w}$=5.6) and will move into the sensor coating from the saliva and other biofluids with a partition coefficient of ~871,000:1. However, unlike the sensors and devices described in U.S. application Ser. No. 13/124,036 (issued as U.S. Pat. No. 9,700,246) and U.S. application Ser. No. 14/404,674 (which describe sensors to be placed in vivo in a subject in a clinical setting to detect the concentration of drugs) embodiments as described herein are suitable to be used in a non-invasive, non-clinical setting.

The first Technical Objective of this project is to demonstrate an EC signal for THC in reagents using an embodiment of the invention (e.g., a biosensor). The methods to be used are described in detail herein, for example in Section 4 below.

Technical Objective 2: Detection of Active and Inactive THC Metabolites by EC Methods The Pharmacokinetics and Pharmacodynamics of *Cannabis* and THC Fresh *cannabis* contains the compound tetrahydrocannabinolic acid (THCA), a carbonylated precursor to the active drug, trans-$\Delta^9$-tetrahydrocannabinol (THC) that does not have any known psychoactive effects. Upon heating (such as by cooking or smoking), THCA is converted into THC (the primary psychogenic agent of *cannabis*) and metabolized by the body into 11-Hydroxy-$\Delta^9$-tetrahydrocannabinol (11-Hydroxy-THC). 11-Hydroxy-THC is also a psychoactive drug, is more potent than THC, and crosses the blood-brain barrier easily (Wall et al., 1983; Matsunaga et al., 1995; Watanabe et al., 1995). Peak THC concentrations are highest after smoking, conversely, 11-Hydroxy-THC/THC ratios are higher after oral administration due to its metabolism by the liver before entering the bloodstream. Smoked *cannabis*, goes directly from the lungs to the brain and is also briefly highly concentrated in the oral mucosa and saliva. 11-Hydroxy-THC is subsequently metabolized to 11-nor-9-carboxy-THC, the metabolite used to test for *cannabis* use in urine. It is not psychoactive and is not a measure of acute use. However, tests that can distinguish between 11-Hydroxy-THC and 11-nor-9-carboxy-THC can help to determine how recently *cannabis* was consumed (see FIG. 5).

As noted above, the utility of EC methods to detect and quantify a specific compound, such as THC, is determined experimentally. While THC itself was recently shown to demonstrate quantifiable EC behavior, the electrochemistry of its active metabolite, 11-Hydroxy-THC, its inactive prodrug THCA and its inactive blood/urinary metabolite 11-nor-9-carboxy-THC is unknown. Determining whether these compounds have detectable EC signals, and whether they can be distinguished from THC and from each other is the second Technical Objective of this project. The ability to distinguish the psychogenically active THC and 11-Hydroxy-THC from inactive metabolic derivatives using EC methods is a key benchmark for the project. It will also be determined whether the inactive carboxy-derivatives are (or can be) excluded from the biosensor membrane, to eliminate them as both biological and electrochemical interferents at the POC by the sensor. Importantly, quantification of the levels of these metabolites will be determined directly, by oxidation of the drug in the oral fluid sample.

Figure 6:
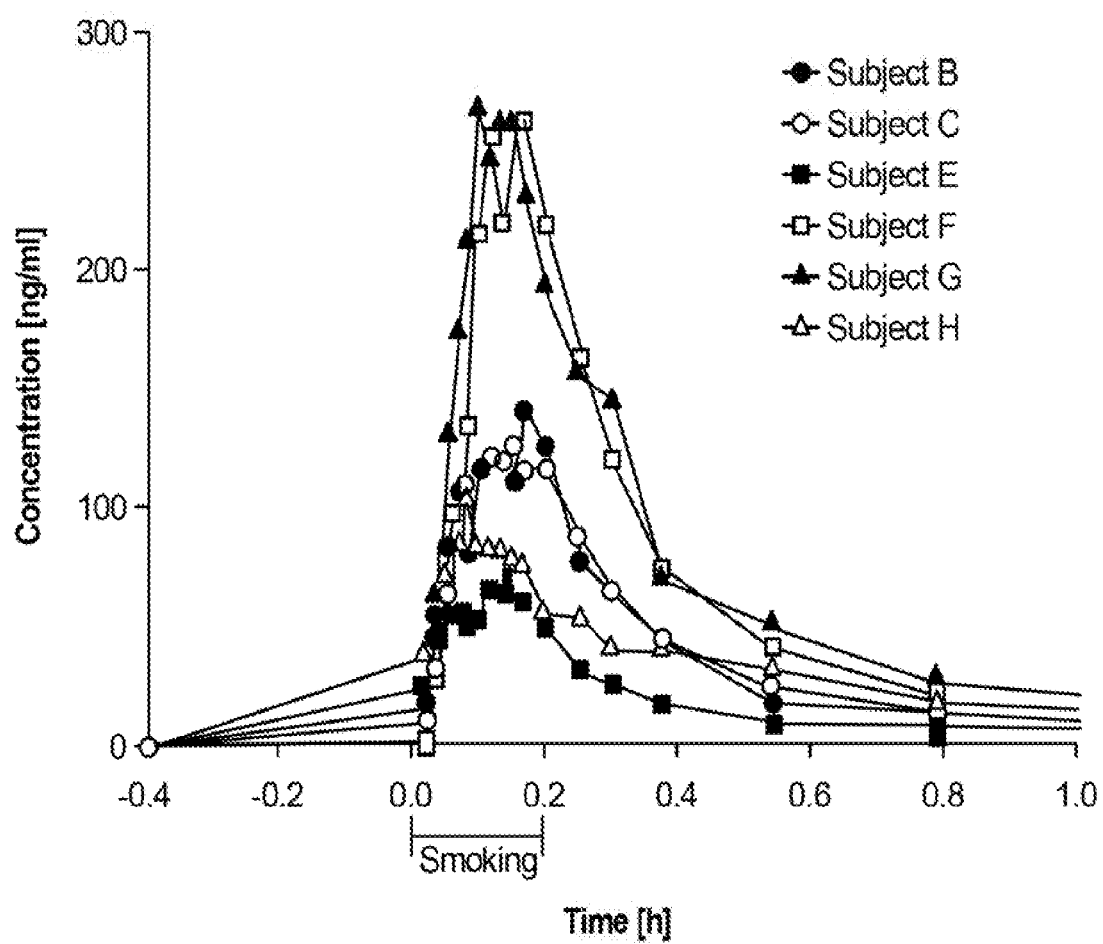
FIG. 6 shows THC blood levels vs. time in a cohort of smokers. THC is rapidly cleared or stored in fat after inhalation of *cannabis* smoke.

Technical Objective 3: Detection of THC and its Metabolites in Biological Fluids Detection of *Cannabis* Use THC has a clearance half-life of less than 30 minutes and is not detectable in urine. Following a dose of THC, the 11-nor-9-carboxy-THC metabolite typically appears in the urine within 1 hour, but can take as long as 4 hours. Conversely, 11-nor-9-carboxy-THC can be secreted in the urine of heavy users for days or even weeks after acute consumption. Thus, this compound is not an indicator for psychogenic impairment in the user, even if found on testing. Other factors that impact psychogenic effects in the user and impairment include; the dose consumed, the detection window used, the percentage of $\Delta^9$-THC in the material consumed, the route of entry (smoking vs. oral), the frequency of use, body fat, and the rate of THC metabolism, which varies from person to person and with chronic use (see FIG. 6).

The membrane-coated biosensor actively partitions hydrophobic drugs from biological fluids into the membrane, permitting EC detection and quantification as described in detail herein. This hydrophobic feature limits the diffusion of hydrophilic molecules, proteins and other components of the blood and other biofluids to minimize biofouling and thus, is a key aspect of both the performance of the sensor for hydrophobic drugs and, importantly, the absence of any requirement for processing of the blood for analysis. This inherent feature permits its use as a POC device to detect and quantify THC in saliva and other biofluids.

Medicolegal Issues of *Cannabis* Testing—Results from the DRUID Project

The Driving under the Influence of Drugs, Alcohol and Medicines (DRUID) Project was European research study in the domain of road safety conducted to provide reference studies of the impact on fitness to drive for alcohol, illicit drugs and medicines. It gave new insights to the degree of impairment caused by psychoactive substances and their impact on road safety. DRUID generated recommendations for the definition of analytical and risk_thresholds, analyzed the prevalence of alcohol and other psychoactive substances in accidents and in general driving, evaluated "good practices" for detection and training measures for police monitoring drivers. Characteristics of drivers under the influence of psychoactive substances were identified, oral fluid screening devices and checklists for identifying clinical signs of impairment were evaluated and a cost-benefit analysis of increased anti-drug enforcement performed.

THC Detection in Saliva

The results of the DRUID study of evaluation of current oral fluid screening methods (chromatographic and monoclonal immunoassays) showed that, for *cannabis* tests, sensitivities ranged from 11% to 59%, with specificities between 90% and 100% and accuracies from 41% to 82%. The results demonstrated that most of the systems to date, which use secondary analytes or immunoassays, are not reliable enough to detect THC with sufficient specificity and sensitivity. The use and validation of conversion factors between plasma, whole blood, and saliva was a major objective of DRUID (FIG. 7). Variations between individuals suggested that conversion factors may not accurately estimate drug levels in blood based on oral samples. However, drug analysis in samples of oral fluid can be used to estimate the drug in blood using the criteria of threshold concentrations. The third Technical Objective of this project is to demonstrate a reliable and quantitative EC signal for the direct measurement of THC in biological fluids (such as saliva, blood) using embodiments of th einvention, such as those comprising a biosensor as described herein.

Technical Objective 4: Comparison with HPLC, MS/LC Methods

Technical Objective 5: Biosensor Performance and Accuracy

The results of the DRUID study above showed limited sensitivity, good specificity, and variable accuracies for current oral *cannabis* tests. The results demonstrated that most of these systems are not reliable enough to detect THC with the sensitivity, specificity, and accuracy if laboratory methods used to measure THC and 11-Hydroxy-THC drug levels by spectrophotometric immunoassays, HPLC, or MS/LC. Coefficients of variation in these laboratory assays range from 4%-17% depending on the method used and the drug being detected. In addition, the minimum limit of detection (DL) is an important metric for determining the sensitivity and reliability of the assay. The level of THC in the blood and oral saliva decreases rapidly after smoking (more gradual after oral use). Metabolism of THC occurs rapidly in the liver microsomes by the enzymes of the cytochrome P450 complex, mainly the CYP2C subfamily. The ratio of THC to 11-OH-THC in plasma can vary between men and women was about (2:1 vs. 1:1) and in some cases concentrations of the metabolite may exceed that of THC. Thus, demonstrating a strong correlation between biosensor measurements and HPLC/MS/LC methods would greatly improve the performance of the device relative to current products and may provide stronger evidence in legal proceedings related to impaired driving. The fourth and fifth Technical Objectives of this project are to demonstrate a comparative quantitative EC signal for the direct measurement of THC in biological fluids (saliva, blood) versus HPLC and MS/LC methods. The performance and accuracy relative to laboratory methods including sensitivity, specificity, accuracy, reproducibility, signal variance and stability, and detection limits will be determined using known doses and/or concentrations of synthetic THC (such as Dronabinol and its related compounds discussed herein) using analytical samples (Cerilliant).

There are three classes of substance thresholds: "Risk thresholds" concentrations in blood that indicate a certain accident risk or impaired driving, "Lower effect limits" the lowest concentration where an effect on driving is observed, and "Limit of detection" or "Limit of quantification" (LOQ) based on technical limitations in order to guarantee a valid and reliable analytical result and avoid false positive results. While the relationship between drug levels and its effect is not linear for most drugs, identifying "Risk thresholds" or "Lower effect limits" may be an appropriate strategy to developing metrics that will meet legal and judicial definitions of potential impairment, similar to blood alcohol level testing. Current laws in WA and CO where *cannabis* use is legal set threshold blood limits for THC at 5 nmol. The LOQ of the biosensor for THC and 11-Hydroxy-THC will be determined. We will also establish the lowest concentration that can be accurately measured, using LOQ as a legal threshold beyond which there is increased risk of impairment. Features of *cannabis* use that relate to developing these metrics include; the acute rise and fall of THC in saliva after smoking, the EC signals for other metabolites (psychogenic and non-psychogenic) which will be determined, the lower detection limit for THC and 11-Hydroxy-THC and the PK of THC and its metabolites in saliva. THC drug hysteresis with respect to behavioral changes is not completely understood. However, once equilibrium is established (~20 minutes), a more direct correlation of THC blood levels and effect is observed.

Technical Objective 6: Biosensor Hardware a Hand Held Device

Numerous products on the EU market (Oratect, OrAlert, Cozart DDVC, others) and startup US companies (e.g., Hound Labs, Cannabix) have or are developing portable oral sampling devices for POC use. These technologies use indirect measures of detection; chromatographic and immunoassays, labeled drug and alternative MS systems, to detect presence of THC in saliva or breath, as a proxy for blood levels. Most have not been validated by the US FDA or DOT.

Embodiments as described herein, such as the THC oral biosensor, will be the only product which directly measures THC levels in biofluids. The biosensor is designed as a single use, sublingual probe (see FIG. 1, which can also be used to collect oral specimens for follow on MS/LC testing as required). The driving electronics are already prototyped and will be housed in a portable, battery operated device, similar in design and function to an oral electronic thermometer (see FIG. 8). The 6$^{th}$ Technical Objective of this project is to prototype a hand held device which can be used to directly measure THC levels in biological fluids (such as saliva, blood) using our proprietary biosensor and potentiostat driver.

Work Plan.

The Deliverables Under the Work Plan Include:

Clinical validation studies of the performance of the biosensor for the detection and quantification of THCA (inactive prodrug), THC and 11-Hydroxy-THC its psychoactive metabolite, and 11-nor-9-carboxy-THC (inactive metabolite) in complex biological solutions including saliva and blood with reports describing experimental protocols and the quantitative results of these studies.

Performance characteristics of the biosensor in saliva and blood (signal fidelity, stability, detection limits, potential EC interferents, and biofouling) using the AFAS laboratory platform (see below).

Performance characteristics of the sensor in the detection of THC and 11-Hydroxy-THC (detection limits, variances) relative to current clinical drug screening assays, HPLC, MS/LC.

The proposed device provides immediate, user specified "real time" quantification of drug levels from a graphical interface in a plug-and-play design that requires no sample preparation.

Work Plan Objectives: Electrochemical Biosensor Prototyping and Testing.

Figure 9:
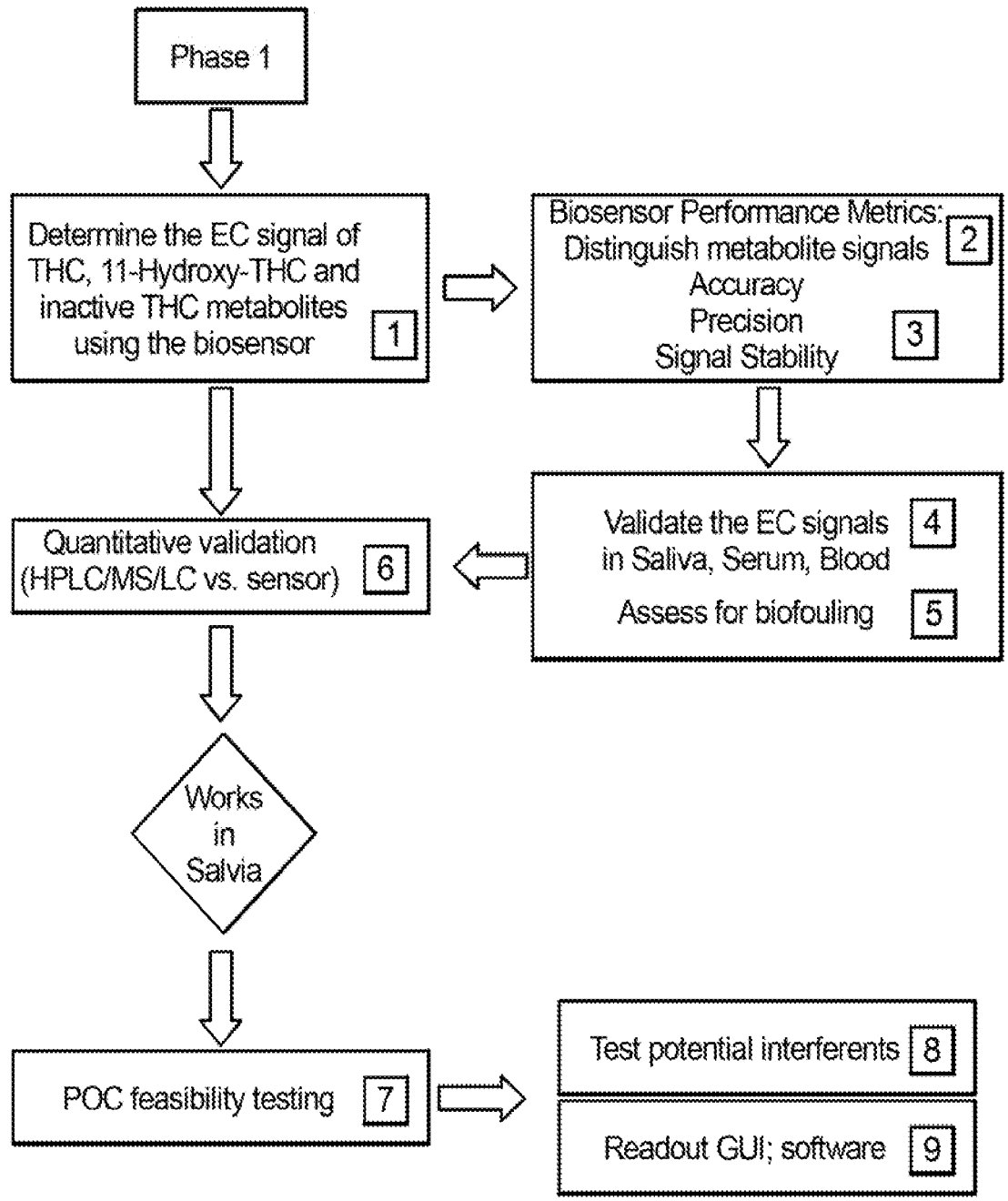
FIG. 9 shows the work plan objectives for electrochemical biosensor prototyping and testing. A schematic overview of the studies and flow process during the Phase I project is shown.

1. Validate the EC Detection and Quantification of THC and its Metabolites Using the Biosensor Cyclic voltammetry (CV) and chronoamperometry (CA) studies will be performed to validate an electrochemical signal for THC using embodiments as described herein. See FIG. 9, Schematic [1]. Performance metrics to be determined in reagent solutions include; optimizing scan rate and voltage for signal detection, determination of sensitivity, detection limits, signal fidelity, error and uncertainty, biofouling (if any) and dynamic range in saline solution and other reagents as previously performed and described in detail below. Synthetic THC (Cerilliant T-005), its inactive prodrug THCA (T-093) and its metabolites 11-Hydroxy-THC (psychoactive, H-026), and 11-nor-9-carboxy-THC (inactive, T-018) will be obtained under a DEA Schedule 1 drug license from Cerilliant analytical reference standards and diluted for use to assure accurate drug concentrations in the proposed studies. See FIG. 9, Schematic [2][3]. Methods to be used are presented in detail in Section 4 and described herein.

CV and CA studies will be performed to determine the presence or absence of an EC signal for THCA (inactive prodrug), 11-Hydroxy-THC (psychoactive metabolite), and 11-nor-9-carboxy-THC (inactive metabolite) in reagents using the biosensor. Performance metrics to be determined include; optimizing scan rate and voltage, determination of sensitivity, dilution limits, signal fidelity over time and dynamic range in saline solutions and reagents. Whether any absence of signal is a function of the electrochemistry versus exclusion by the membrane coating will be determined by performing similar experiments in aqueous and organic reagents using uncoated electrodes. See FIG. 9, Schematic [4]. The detection limit will be targeted in the 5 nM range (CO and WA legal limits) and the dynamic range determined for THC. Biofouling will be assessed using the methods described below. See FIG. 9, Schematic [5].

Validate Biosensor Performance Compared to HPLC and MS/LC Methods

The signal correlation will be determined in complex biological fluids containing THC and serum or blood. Additional studies including potential clinical interferents, 4-acetamidophenol (Tylenol) and ascorbic acid (vitamin C), will be performed to determine whether the correlations between EC and HPLC methods seen for propofol are similarly seen for the detection of THC and its metabolites. See FIG. 9, Schematic [6][8]. The drugs will be extracted from the fluid using an organic reagent. The reagent containing the extracted drug is then processed using two independent and methodologically distinct HPLC procedures to quantify drug in serum containing solutions, 1) precipitation with subsequent centrifugation in ethanol, and 2) solid phase extraction and elution with methanol. A strong correlation between the two methods (as is shown for propofol, described herein) will confirm that the biosensor is correlated with the "gold standard" HPLC method measurements, even in the presence of clinical interferents with similar molecular structures.

2. Detection of THC and its Metabolites in Biological Fluids—AFAS Flow System

The Automated Flow Analysis System (AFAS) is implemented as the flow control component of either an open-loop or closed-loop configuration. Drug concentrations are measured using a coated biosensor in an encasement manifold including reference electrodes as described in detail above. Fluid volume and flow within the system can be controlled to deliver either, 1) known drug levels to the sensor to measure variances in the drug levels quantified (sensitivity and reproducibility) or 2) to simulate drug metabolism pharmacokinetics (PK) and dilution over time (applied to model drug metabolism), which can be varied according to the published PK. This flow through channel provides a method to deliver rapid, stepwise changes in analyte concentration, facilitating both steady state and dynamic characterization of sensor performance in a simulated in vivo environment. Response time and signal integrity of biosensor is determined by changes in drug concentration using both increasing and decreasing stepwise changes.

Pharmacokinetic Modeling

Figure 10:
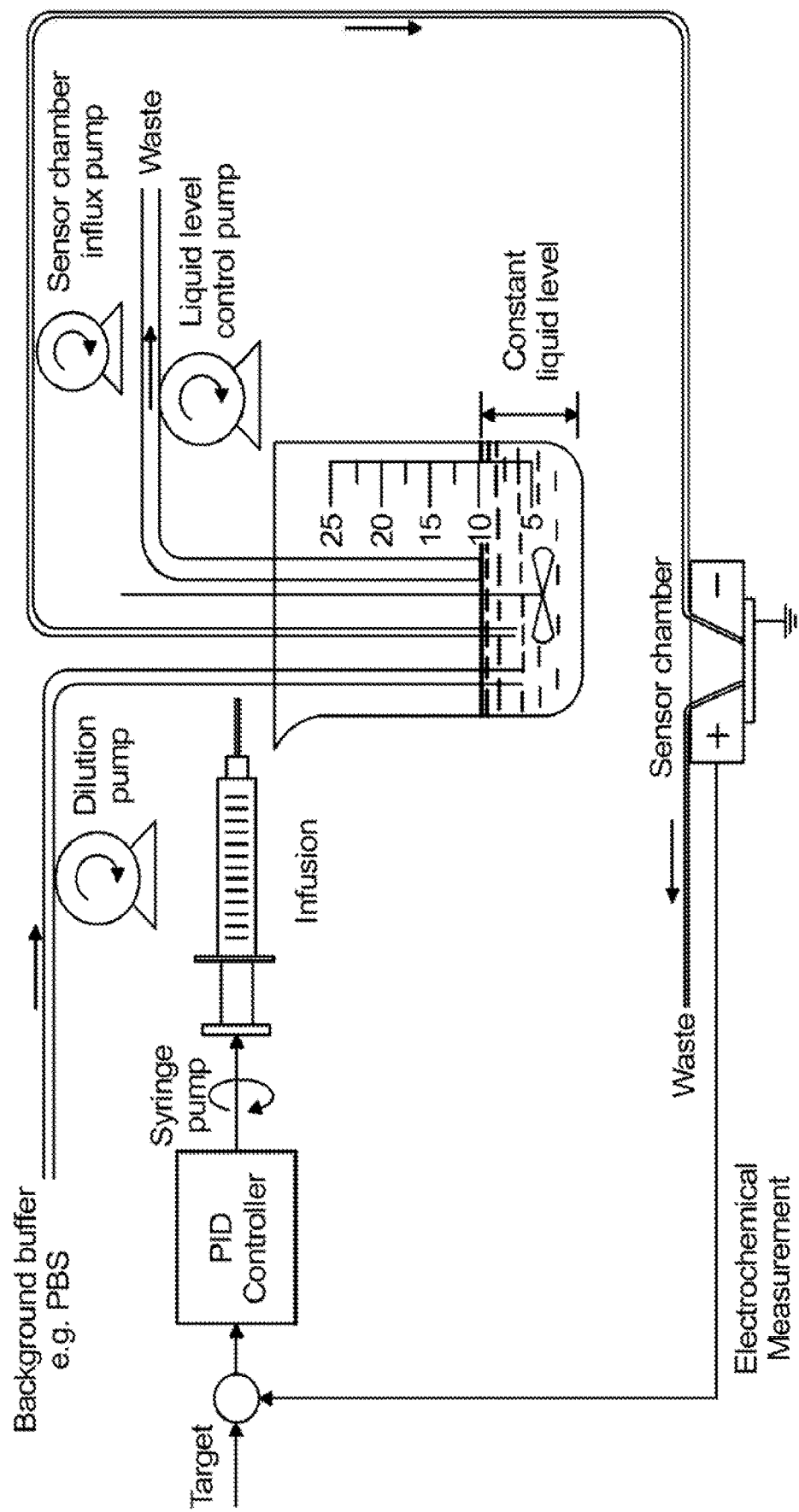
FIG. 10 shows experiment setup for testing the concentration of drug measured by the biosensor in a simulated "patient". The concentration of the drug can be modulated in real time and clinical PK/PD simulated for known drug metabolism.

The experimental setup used to simulate the concentration decay in a single compartment model is shown in FIG. 10. A beaker with a given volume represents the first compartment, which is also called dilution chamber. The liquid volume inside the beaker is held constant. The content of the beaker is continuously diluted by steady flow of PBS (or complex biological media such as saliva or blood) into the beaker. To mimic the PK drug concentration decay, the dilution chamber can be tuned by varying the volume of the chamber and the dilution rate. The dilution rate will be set by a programmable peristaltic pump. A constant solution level in the dilution chamber is set via the combination of a suction pump and tube. The inlet of the suction tube is set to the desired solution level while the other end of the tube is attached to the suction pump. The flow rate of the suction is always faster than the dilution flow into the chamber, which prevents the solution level from rising above the inlet of the suction tube. The content of the chamber is recirculated with an additional pump, which transports the fluid through the EC flow cell for replicate concentration measurements. See FIG. 9, Schematic [4][5].

The planar biosensor resides in manifold with a circular opening in the centers and aligned with the input and output ports. This flow through channel provides a method to deliver rapid analysis of drug concentration and will be used to validate sensor performance in a simulated roadside environment. Optimization of signal detection and quantification, and potential for biofouling in real time will be experimentally determined using our methods. The CA current will be continuously recorded during the duration of the experiment. This CA mode has the advantage of low residual current (noise) which permits a lower detection limit. This bench top closed-loop system permits us to model the performance of the biosensor in a model "patient". The CA mode has the advantage of low residual current (noise) for low detection limit. The sample plug passes the flow-through detector cell with the sensor and a dose-dependent, transient signal is recorded. The technical components of the prototype shall be integrated to establish that they will work together to demonstrate a "high fidelity" system, a TRL5 designation.

Biosensor Performance and Accuracy, Limit of Detection—Methods

As we have shown herein, the limit of detection as the smallest concentration (or quantity) that can be detected in an analytical procedure with a given certainty. This concentration is derived from the mean of the measured signal in the blank ($\bar{x}_{bi}$), the standard deviations of the blank measurement ($s_{bi}$) and the slope of the analytical calibration curve (S) as $c_{DL}^{1}=(x_L-\bar{x}_{bi})/S$, where $x_L=\bar{x}_{bi}+3s_{bi}$.

The detection limit for drug determination with the membrane-coated sensor in cyclic voltammetric experiments by considering the standard deviation of the background current recorded in repeated CV scans. The resolution of the measurement is defined as the minimum difference between two concentrations that can be distinguished with a given probability. The resolution of the measurements ($c_{DL}^{2}$) in this work has been calculated as $c_{DL}^{2}=3\times RMSD/S$. This method will be used to determine the response range, detection limit ($c_{DL}^{1}$) and resolution ($c_{DL}^{2}$) values for the target antibiotics with our plasticized membranes.

The calculation of the membrane/water partition coefficient requires the knowledge of the diffusion coefficient of the solute in the membrane. The sensitivity and selectivity of the membrane-coated working electrode for the hydrophobic antibiotics is influenced by the dielectric properties of the plasticizer, the selection and concentration of the background electrolyte, and the incorporation of mobile cation-exchange sites into the membrane. These components have been optimized for propofol but are experimentally variable. The membrane composition also affects the peak potential at which the drug is oxidized in the membrane. Diffusion coefficients in the membrane will be determined for THC and 11-Hydroxy-THC using this method. Methods and previous data are described in detail below.

3. Biosensor Hardware—Hand Held POC Device and Communications Interface

The electronics and readout display is designed as a small portable, handheld potentiostat that can be applied for amperometric measurements at a fixed potential as well as voltammetric measurements. LabView protocols developed to communicate with the potentiostat will be used to drive the biosensor and measure the current (drug level) read by the sensor. See FIG. 9, Schematic [7]. This protocol will be incorporated into the prototyped chip shown in FIG. 10. Embedded software is provided by the manufacturer. The instrument is battery powered but designed with a USB connection to port to a laptop computer. These devices have appropriate current ranges for our application: 1 nA to 100 µA, with a resolution of 1 pA. The concept of the "roadside" device is shown, a handheld device with readout (can also include a printer for documentation or Bluetooth connection), single use biosensor for sublingual placement (like a common electronic thermometer) and circuit design with multiple, independent sensors to obtain replicate measurements (FIG. 11).

Relationship with Future Research and Development

As described herein, embodiments of the invention can detect and quantify THC. The electrochemistry of $\Delta^9$-THC has been reported using several electrochemical methods (Nissim 2015; Balbino et al., 2014; Novak et al. 2013). This includes the ability to detect THC at the level of 25-50 ng/mL in undiluted saliva (Wanklyn, et al. 2016).

As discussed herein, the utility of EC methods to detect and quantify specific compounds, such as THC metabolites, is determined experimentally. While THC itself was shown to demonstrate quantifiable EC behavior, the electrochemistry of its active metabolite, 11-Hydroxy-THC, its inactive prodrug THCA and its inactive blood/urinary metabolite 11-nor-9-carboxy-THC are not yet known. Determining whether these compounds have detectable EC signals, and whether they can be distinguished from THC and from each other are important aspects of this invention. For example, the ability to distinguish the active psychogenic THC and 11-Hydroxy-THC molecules from inactive metabolic derivatives using EC methods is a key benchmark for the project. Further, the inactive 11-nor-9-carboxy-THC must be distinguishable from both THC and 11-Hydroxy-THC, since it is an inactive compound and its presence is not necessarily an indication of impairment. Studies will determine whether the inactive carboxy-derivatives have an EC signal that can be distinguished or are (or can be) excluded from the biosensor membrane, to eliminate them as both biological and electrochemical interferents at the POC by the sensor.

After determination of the EC signal of these compounds, initial validation studies of biosensor performance in biological fluids and its accuracy and detection limits relative to HPLC and MS/LC methods will be determined. Sublingual device for clinical use will also be prototyped. Embodiments can comprise the driving electronics and software, modified as required from our current potentiostat software, based upon the THC studies.

Potential Use by the Federal Government

The National Highway Traffic Safety Administration (NHTSA), under the USDOT was established to carry out safety programs under the National Traffic and Motor Vehicle Safety and Highway Safety Acts of 1966. NHTSA is responsible for reducing deaths, injuries and economic losses not only from motor vehicle crashes through safety and performance standards but also charged with helping states and local communities to reduce the threat of impaired drivers. The NHTSA actively conducts research on driver behavior to develop the efficient and effective means of bringing about traffic safety improvements.

Decreasing crashes, injuries, and fatalities from impaired driving is a priority for NHTSA. As states move toward legalizing medicinal and recreational use of marijuana, there may be increased use of this drug by drivers. Determination that a drug (especially THC) is present in the body of a suspected drug impaired driver presents challenges for law enforcement, especially in conducting and obtaining results from any type of test close-in-time to the driving event. Use of blood tests to determine the presence of a drug (especially THC) in the body can be time consuming and require a warrant, presenting challenges for law enforcement and prosecution. This may result in some individuals continuing to drive impaired by marijuana (or other drugs). The DRUID study collected data on the prevalence of psychoactive substance use in the general driving population in 13 European countries. Risk estimates for driving under influence of psychoactive substances were derived from the case-control study in which data from roadside surveys was linked to the data from approximately 4,500 drivers seriously injured or killed in an accident. The characteristics of drivers tending to drive under the influence of psychoactive substances were identified.

The DRUID accident risk studies demonstrated a two-fold increased risk of fatal accidents in which the driver tested positive for *cannabis* and the combined use of alcohol and *cannabis* increased the risk of causing a fatal accident 15-fold. Thus, the detection of *cannabis* use in active drivers through the use of on-site screening devices greatly increases the effectiveness of drugged-driving enforcement to improve highway safety for all drivers and will be enhanced by POC use of *cannabis* detecting devices. A device that can detect the presence of THC and its psychogenic metabolites at the POC would provide law enforcement officers and prosecutors with crucial information about potential impairment and also aid in decisions whether to pursue impaired driving charges by providing reliable evidence of quantitative drug levels in the driver. A portable device, similar to an alcohol breathalyzer testing device, would be an ideal tool for law enforcement, i.e., an innovative technology to determine the presence of THC in the body that is accurate and reproducible, easy to administer, and minimally intrusive. The approval of such a point-of-contact device to detect the use of and presence of psychogenic agents in drivers would be of significant value to the NHTSA and the law enforcement officers responsible for assuring the safety of public highways.

REFERENCES CITED IN THIS EXAMPLE

Alozie S O, Martin B R, Harris L S, et al. 3H-delta 9-Tetrahydrocannabinol, 3H-cannabinol and 3H-cannabidiol: penetration and regional distribution in rat brain. Pharmacol Biochem Behav 1980; 12: 217-21.
Balbino M A, Eleoterio I C, de Oliveira L S, de Menezes M M T, de Andrade J F, Ipolito A J, de Oliveira M F. A comparative study between two different conventional working electrodes for detection of $\Delta^9$-tetraydrocannabinol using square-wave voltammetry: a new sensitive method for forensic analysis. J Braz Chem Soc. 2014; 25:589-596.
Kivlehan F A, Garay F, Guo J, Chaum E, Lindner E. Towards feedback-controlled anesthesia: Voltammetric measurement of propofol in serum-like electrolyte solutions. Anal Chem. 2012, 84(18):7670-6.
Kivlehan F, Chaum E, Lindner E. Propofol Detection and Quantification in Human Blood: The Promise of Feedback Controlled, Closed-loop Anesthesia. Analyst, 2014, 140(1):98-106.
Langmaier J, Garay F, Kivlehan F, Chaum E, Lindner E. Electrochemical Quantification of 2,6-Diisopropylphenol (Propofol), Analytica Chimica Acta, 2011, 704:63-67.
Matsunaga T, Iwawaki Y, Watanabe K, et al. Metabolism of delta 9-tetrahydrocannabinol by cytochrome P450 isozymes purified from hepatic microsomes of monkeys. Life Sci 1995; 56 (23-24): 2089-95.
Nissim R, Compton R G. Absorptive stripping voltammetry for *cannabis* detection. Chem Cent J. 2015; 9:41.
Novak I, Mlakar M, Komorsky-Lovric S. Voltammetry of immobilized particles of cannabinoids. Electroanalysis. 2013; 25:2631-2636.
P&S Market Research (2015) Global industry insight: drugs of abuse testing market development and demand forecast to 2020.
Rainey F, Kivlehan F, Chaum E, Lindner E. Toward Feedback Controlled Anesthesia: Automated Flow Analytical System for EC Monitoring of Propofol in Serum Solutions. Electroanalysis, 2014, 26:1295-1303.
Wall M E, Sadler B M, Brine D, et al. Metabolism, disposition, and kinetics of delta-9-tetrahydrocannabinol, in men and women. Clin Pharmacol Ther 1983; 34 (3): 352-63
Wanklyn C, Burton D, Enston E, et al. Disposable screen printed sensor for the electrochemical detection of delta-9-tetrahydrocannabinol in undiluted saliva. *Chemistry Central Journal*. 2016; 10:1.
Watanabe K, Matsunaga T, Yamamoto I, et al. Involvement of CYP2C in the metabolism of cannabinoids by human hepatic microsomes from an old woman. Biol Pharm Bull 1995; 18(8): 1138-41.

EQUIVALENTS

Those skilled in the art will recognize, or be able to ascertain, using no more than routine experimentation, numerous equivalents to the specific substances and procedures described herein. Such equivalents are considered to be within the scope of this invention, and are covered by the following claims.

What is claimed:

1. A non-invasive device for detecting at least one electrochemically active molecule in a fluid sample of a subject, the device comprising a non-invasive, electrochemical, voltammetric sensor comprising two or more electrodes, wherein at least one end of the electrodes is in direct contact with a water-immiscible coating which has hydrophobic properties and is configured to selectively partition the electrochemically active molecule from the fluid sample, wherein a voltammetric signal is generated sublingually by the sensor in the presence of an electrochemically active molecule in the fluid sample, wherein the sensor comprises a sublingual sensor.

2. The device of claim 1 further comprising
a non-invasive sensing unit and a control unit;
wherein the sensing unit comprises an electrochemical, voltammetric sensor;
wherein the control unit comprises one or more of a user interface, output
element, controller, peripherals, power supply, external communications, and
subject interface; and
wherein the sensing unit is in communication with the control unit.

3. The device of claim 2, wherein the sensing unit is disposable.

4. The device of claim 1, wherein the sensor communicates the voltammetric signal to the control unit, and wherein the output element of the control unit indicates the voltammetric signal, the presence of the molecule in the sample, the concentration of the molecule in the sample, the identification of the molecule in the sample, or a combination thereof.

5. The device of claim 1, wherein the electrochemical, voltammetric sensor comprises two or more electrodes oriented in parallel.

6. The device of claim 1, wherein the electrodes comprise carbon, glassy carbon, silver, mercury, gold, platinum, palladium, ruthenium, or a combination thereof.

7. The device of claim 1, wherein the electrodes comprise a working electrode, a reference electrode, a counter electrode, or any combination thereof.

8. The device of claim 7, wherein the working electrode comprises carbon, the reference electrode comprises silver, the counter electrode comprises platinum, or any combination thereof.

9. The device of claim 1, wherein the water-immiscible coating comprises a structural component, a water-immiscible organic solvent, a charge transfer component, or any combination thereof.

10. The device of claim 9, wherein the structural component comprises polyvinylchloride (PVC), silicone rubber, polyurethane, acrylate polymer, polypyrrole, polythiophene, polyoctylthiophene, polyanaline, polyvinyl pyrrolidone, and combinations thereof.

11. The device of claim 9, wherein the water-immiscible organic solvent comprises 2-nitrophenyl octyl ether (o-NPOE), dioctyl sebacate (DOS), bis(2-ethylhexyl) sebacate, benzyl 2-nitrophenyl ether, bis(1-butylpentyl) adipate, bis(2-ethylhexyl) adipate, bis(2-ethylhexyl) phthalate, 1-chloronaphthalene, chloroparaffin, 1-octanol, 1-decanol, dibutyl phthalate, dibutyl sebacate, dibutyl-dilaurate, dodecyl 2-nitrophenyl ether, and combinations thereof.

12. The device of claim 9, wherein the charge transfer component comprises tetradodecylammonium tetrakis(pentafluorophenyl)borate (TDDATPFPhB), tetrahexylammonium perchlorate, or a combination thereof.

13. The device of claim 9, wherein the coating further comprises an adhesion enhancing component, a biocompatibility enhancing component, a membrane-resistance controlling component, and ion-exchange component, or a combination thereof.

14. The device of claim 9, wherein coating comprises about 15 to about 67 wt percent structural component, about 33 to about 85 wt percent water-immiscible organic solvent, and about 0.001 to about 15 wt percent charge transfer component.

15. The device of claim 14, wherein the structural component is PVC, the water-immiscible organic solvent is o-NPOE, and the charge transfer component is TDDATPFPhB.

16. The device of claim 1, wherein the sample comprises a biological fluid.

17. The device of claim 16, wherein the biological fluid comprises a volume sufficient to immerse the sensor or a portion thereof.

18. The device of claim 16, wherein the volume of the biological fluid comprises about 10 µl or less.

19. The device of claim 16, wherein the biological fluid comprises blood, urine, saliva, tears, lavage or sweat.

20. The device of claim 1, wherein the coating or a portion thereof is in direct contact with the sample.

21. The device of claim 20, wherein the portion comprises at least about 25%, at least about 50%, at least about 75%, at least about 100% of the coating.

22. The device of claim 1, wherein the coating actively partitions the electrochemically active molecule from the sample, wherein the electrically active molecule is hydrophobic, lipophilic, or both.

23. The device of claim 22, wherein the molecule has a log Po/w value of about 4 to about 12.

24. The device of claim 22, wherein the molecule has a partition coefficient of about 871,000:1 in a biological fluid.

25. The device of claim 22, wherein the molecule has a log Po/w value of about 0 to about 5, about 5 to about 10, about 10 to about 15, or greater than about 15.

26. The device of claim 1, wherein the coating limits the partitioning of at least one molecule in the sample, wherein the molecule whose partitioning is limited is hydrophilic, not hydrophobic, not lipophilic, or a combination thereof.

27. The device of claim 1, wherein the molecule comprises at least one molecule from the *Cannabis* plant, a metabolite thereof, or a combination of both.

28. The device of claim 27, wherein the metabolite of THCA comprises $\Delta^9$-tetrahydrocannabinol (THC), 11-hydroxy-$\Delta^9$-tetrahydrocannabinol (11-hydroxy-THC), and 11-nor-9-carboxy-tetrahydrocannabinol (11-nor-9-carboxy-THC).

29. The device of claim 1, wherein the molecule comprises the general structure:

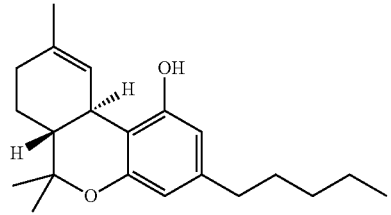 [SMILES: CCCCCc1cc(O)c2c(c1)OC(C)(C)[C@@H]1CCC(C)=C[C@@H]21]

30. The device of claim 1, wherein the molecule comprises tetrahydrocannabinolic acid (THCA), a metabolite of THCA, a prodrug of THCA, or a combination thereof.

31. The device of claim 1, wherein the sample comprises an unprocessed sample.

32. A method for detecting at least one molecule in a sample of a subject, the method comprising contacting the sample with the electrochemical, voltammetric sensor of the device of claim 1 for a period of time sufficient to generate a voltammetric signal, wherein the voltammetric signal correlates to the presence of the molecule in the sample, the identity of the molecule in the sample, the concentration of the molecule in the sample, or a combination thereof.

33. A method for identifying at least one molecule in a sample of a subject, the method comprising contacting the sample with the electrochemical, voltammetric sensor of the device of claim 1 for a period of time sufficient to generate a voltammetric signal, wherein the voltammetric signal correlates to the identification of the molecule in the sample.

34. The method of claim 32 or 33, wherein the period of time comprises less than about 5 minutes.

35. The method of claim 32 or 33, wherein the period of time comprises less than about 1 minute.

\* \* \* \* \*